United States Patent [19]
Guyton et al.

[11] Patent Number: 6,027,216
[45] Date of Patent: Feb. 22, 2000

[54] EYE FIXATION MONITOR AND TRACKER

[75] Inventors: David Lee Guyton; David George Hunter, both of Baltimore, Md.; Saurabh Navinchandra Patel, Monmouth Junction, N.J.; Julie Christine Sandruck, Rochester, N.Y.; Robert Lee Fry, New Windsor, Md.

[73] Assignee: The Johns University School of Medicine, Baltimore, Md.

[21] Appl. No.: 09/172,842

[22] Filed: Oct. 15, 1998

Related U.S. Application Data

[60] Provisional application No. 60/062,912, Oct. 21, 1997.

[51] Int. Cl.[7] ............................................. A61B 3/10
[52] U.S. Cl. ............................................. 351/200
[58] Field of Search .................................. 351/200, 204, 351/211, 212, 222, 224, 246

[56] References Cited

U.S. PATENT DOCUMENTS

| | | |
|---|---|---|
| 3,462,604 | 8/1969 | Mason . |
| 3,473,868 | 10/1969 | Young et al. . |
| 3,724,932 | 4/1973 | Cornsweet et al. . |
| 4,145,122 | 3/1979 | Rinard et al. . |
| 4,586,796 | 5/1986 | Molteno . |
| 4,589,776 | 5/1986 | Carver et al. . |
| 4,702,575 | 10/1987 | Breglia . |
| 4,729,652 | 3/1988 | Effert . |
| 4,735,498 | 4/1988 | Uddén et al. . |
| 4,836,670 | 6/1989 | Hutchinson . |
| 4,854,694 | 8/1989 | Hirano et al. ............... 351/224 |
| 4,856,891 | 8/1989 | Pflibsen et al. . |
| 4,989,968 | 2/1991 | Freedman . |
| 5,152,295 | 10/1992 | Kobayashi et al. . |
| 5,177,511 | 1/1993 | Feuerstein et al. . |
| 5,220,361 | 6/1993 | Lehmer et al. . |
| 5,268,711 | 12/1993 | Poxleitner et al. . |
| 5,293,187 | 3/1994 | Knapp et al. . |
| 5,293,535 | 3/1994 | Sensui . |
| 5,303,709 | 4/1994 | Dreher et al. . |
| 5,327,191 | 7/1994 | Shindo et al. . |

(List continued on next page.)

OTHER PUBLICATIONS

Robinson (1963) "A Method of Measuring Eye Movement Using a Scleral Search Coil in a Magnetic Field", *IEEE Transactions on Bio–Medical Electronics* 10(3):137–145.

(List continued on next page.)

*Primary Examiner*—George Manuel
*Attorney, Agent, or Firm*—Alston & Bird LLP

[57] ABSTRACT

Apparatus and method are provided for assessing the direction of fixation of an eye by detecting polarization-related changes in light retroreflected from the fundus of the eye. Nerve fibers in the retina of the eye are birefringent and alter the polarization state of light traversing them as a function of their orientation. The nerve fibers are arrayed in a characteristic pattern in the retina, specifically radiating outward from the fovea and converging to the optic nerve head. By assessment of polarization-related changes in retroreflected light from multiple retinal areas either sequentially or simultaneously, characteristic birefringence signatures of portions of the retina can be identified which are used to assess the direction of fixation of the eye. In addition, interference from the corneal birefringence is reduced by using incident light having a polarization state that is substantially independent of meridional direction. Circularly polarized light or non-polarized light is used for the assessment. Interference from the corneal birefringence is reduced still further by detecting polarization-related changes that are substantially independent of the meridional direction of the corneal birefringence. This is accomplished by detecting changes in ellipticity by measuring solely the Stokes parameter $S_3$ or by measuring any two Stokes parameters. An alternative is measuring the overall intensity of the retroreflected light when the dichroism of the lutein pigment particles in the vicinity of the fovea is used for the assessment.

64 Claims, 17 Drawing Sheets

U.S. PATENT DOCUMENTS

| | | |
|---|---|---|
| 5,331,149 | 7/1994 | Spitzer et al. . |
| 5,345,281 | 9/1994 | Taboada et al. . |
| 5,382,989 | 1/1995 | Uomori et al. . |
| 5,442,412 | 8/1995 | Frey et al. . |
| 5,485,229 | 1/1996 | Hare . |
| 5,576,780 | 11/1996 | Yancey . |
| 5,583,335 | 12/1996 | Spitzer et al. . |
| 5,652,641 | 7/1997 | Konishi . |
| 5,787,890 | 8/1998 | Reiter et al. . |
| 5,882,301 | 3/1999 | Yoshida ................................ 600/318 |

OTHER PUBLICATIONS

Plesch et al. (1987) "Digital Laser Scanning Fundus Camera", *Applied Optics* 26(8):1480–1486.

Young et al. (1975) "Survey of Eye Movement Recording Methods", *Behavior Research Methods& Instrumentation* 7(5):397–429.

Collewijn et al. (1975) "Precise Recording of Human Eye Movements", *Vision. Res.* 15:447–450.

Cornsweet et al. (1973) "Accurate Two–Dimensional Eye Tracker Using First and Fourth Purkinje Images", *Journal of the Optical Society of America* 63(8):921–928.

Reulen et al. (1988) "Precise Recording of Eye Movement: The IRIS Technique Part 1", *Medical & Biological Engineering & Computing* 26(1):20–25.

Wornson et al. (1987) "Fundus Tracking with the Scanning Laser Ophthalmoscope", *Applied Optics* 26(8):1500–1504.

klein Brink et al. (1988) "Birefringence of the Human Foveal Area Assessed in vivo with Mueller–Matrix Ellipsometry", *J. Opt. Soc. Am. A.* 5(1):49–57.

Dreher et al. (1992) "Spatially Resolved Birefringence of the Retinal Nerve Fiber Layer Assessed with a Retinal Laser Ellipsometer", *Applied Optcis* 31(19):3730–3735.

Weinreb et al. (1995) "Scanning Laser Polarimetry to Measure the Nerve Fiber Layer of Normal and Glaucomatous Eyes", *American Journal of Ophthalmology* 119(5):627–636.

Vrabec (1966) "The Temporal Raphe of the Human Retina", *American Journal of Ophthalmology* 62(5):926–938.

Weinreb et al. (1990) "Histopathologic Validation of Fourier–Ellipsometry Measurements of Retinal Nerve Fiber Layer Thickness", *Arch Ophthalmol* 108(4):557–560.

Dodt et al. (1900) "Visually Evoked Potentials in Respense to Rotating Plane–Polarized Blue Light", *Ophthalmic Res* 22:391–394.

Hochheimer et al. (1982) "Retinal Polarization Effects", *Applied Optics* 21(21):3811–3818.

Guyton et al. (1987) "Remote Optical Systems for Ophthalmic Examination and Vision Research", *Applied Optics* 26(8):1517–1526.

Sliney et al. (1980) "Current Laser Exposure Limits", Chapter 8, *Safety With Lasers and Other Optical Sources,* Plenum Press, New York, pp. 261–283.

Blokland et al. (1987) "Corneal Polarization in the Living Human Eye Explained with a Biaxial Model", *J. Opt. Soc. Am. A* 4(1):82–90.

PCT International Search Report, PCT/US98/22122, dated Jan. 29, 1999.

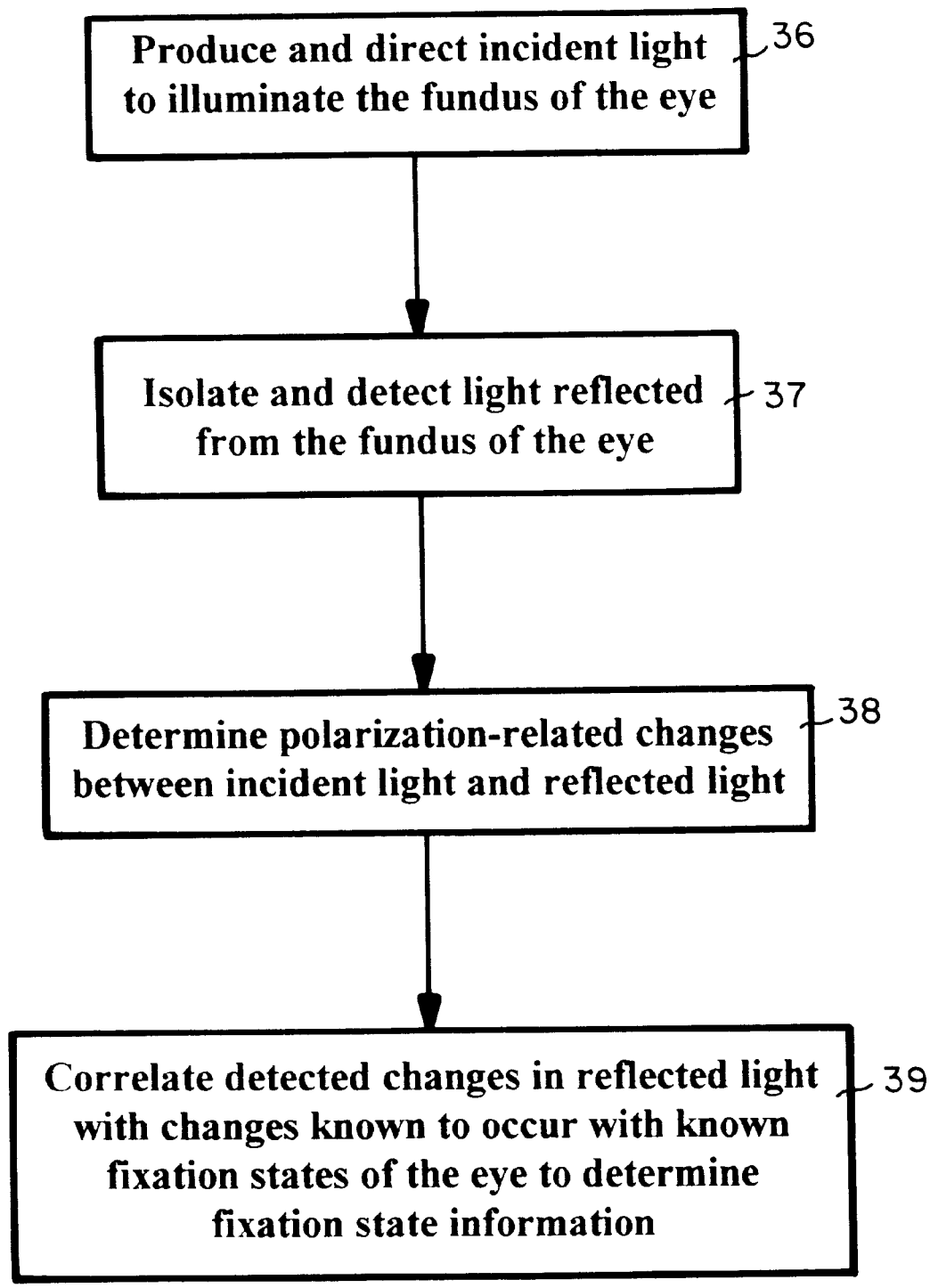
F I G. 4a

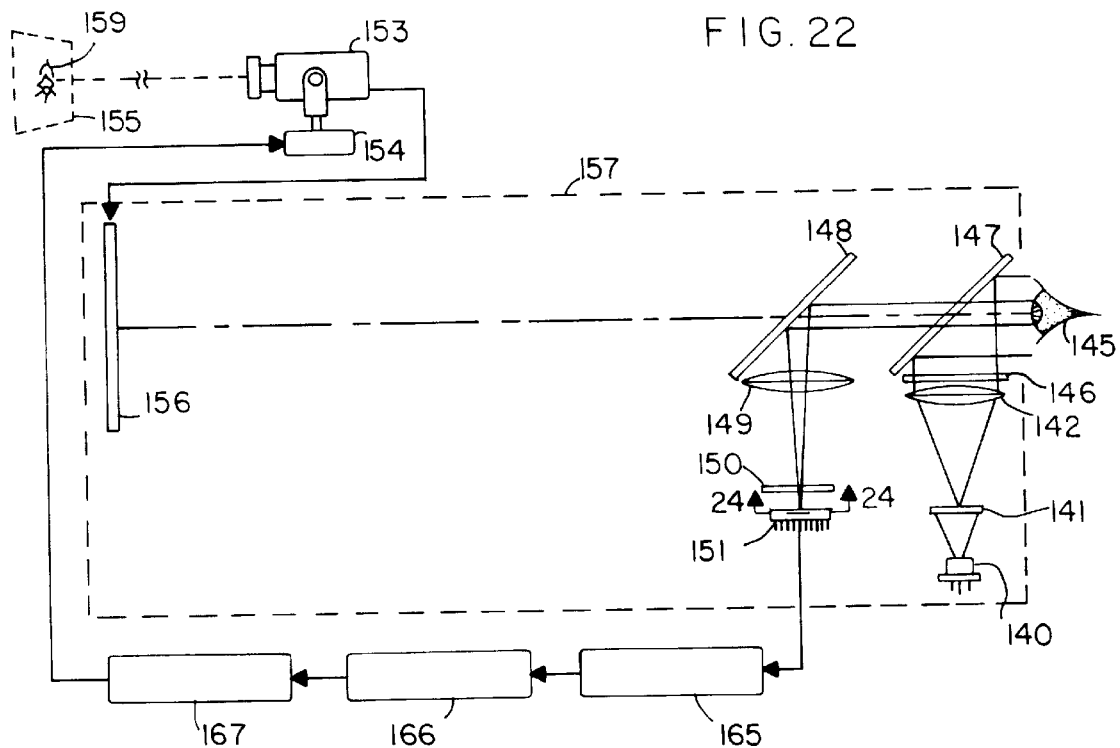
FIG. 22
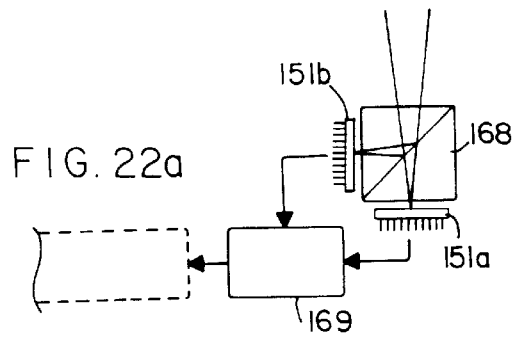
FIG. 22a
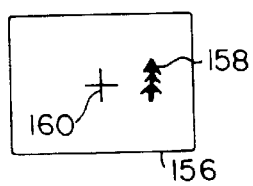 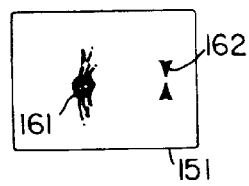 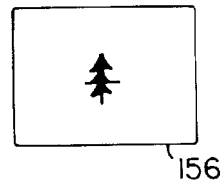 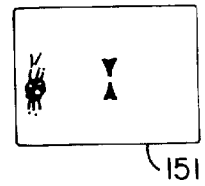
FIG. 23  FIG. 24  FIG. 25  FIG. 26

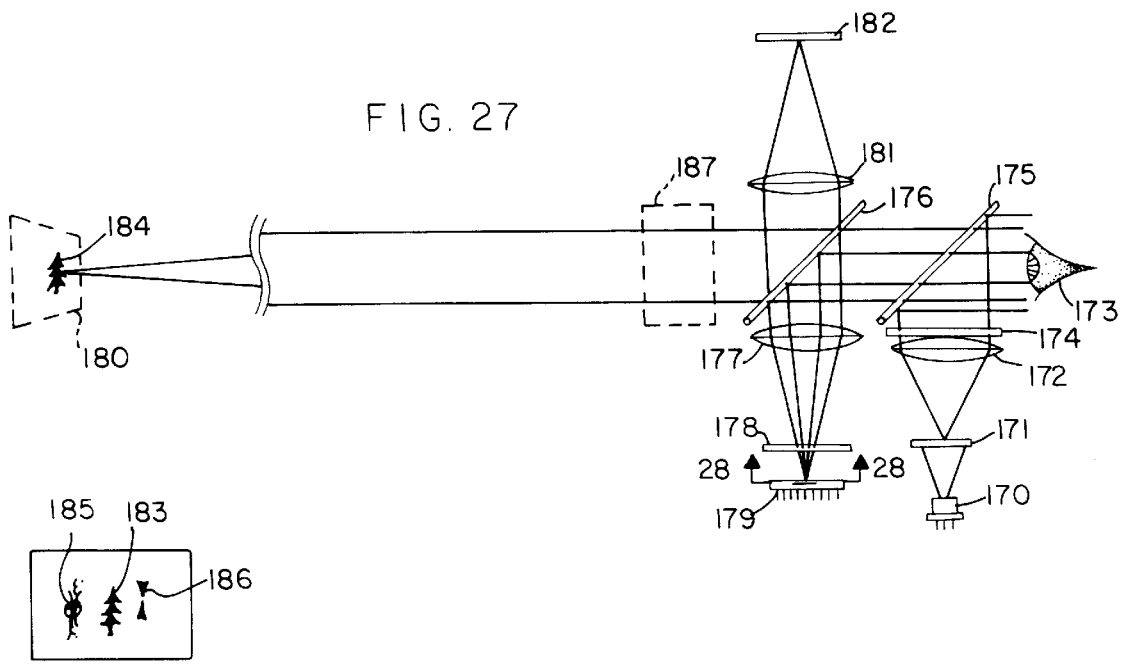
FIG. 27
FIG. 28
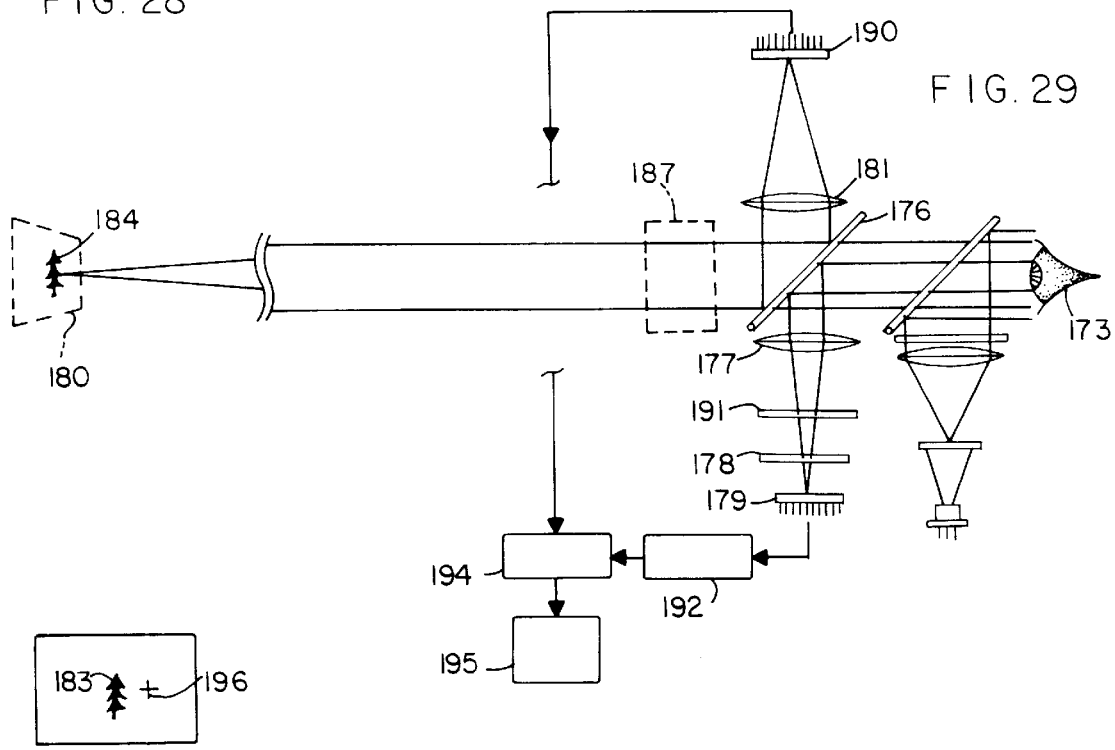
FIG. 29
FIG. 30

EYE FIXATION MONITOR AND TRACKER

CROSS-REFERENCE TO RELATED APPLICATION

This application claims the benefit of U.S. Provisional Application Ser. No. 60/062,912, filed Oct. 21, 1997, the contents of which are herein incorporated by reference.

FEDERALLY SPONSORED RESEARCH OR DEVELOPMENT

This invention was made with Government support under grants EY06447 and RR08058 from the National Institutes of Health. The Government may have certain rights to this invention.

FIELD OF THE INVENTION

This invention relates to ophthalmic devices and, more specifically, to a method and apparatus for assessing the direction of fixation of an eye by using a photodetection system to analyze polarization-related changes in light reflected from the fundus of the eye.

BACKGROUND OF THE INVENTION

Numerous methods have been used to monitor or track the direction of fixation of the eye. Infrared light emitters and sensors attached to glasses frames or to helmets have been used to detect changing infrared light patterns as the eye moves about (see, for example, U.S. Pat. Nos. 3,473,868 (Young et al.), 4,145,122 (Rinard et al.), 4,702,575 (Breglia), 4,735,498 (Udden et al.), 5,345,281 (Taboada et al.), and 5,382,989 (Uomori et al.)).

Video-based eye trackers and fixation monitors have been used to image the corneal light reflection against the background of the pupil of the eye. The position of the corneal light reflection within the image of the pupil yields an indication of the direction of fixation of the eye (see, for example, U.S. Pat. Nos. 3,462,604 (Mason), 4,836,670 (Hutchinson), 5,220,361 (Lehmer et al.), 5,327,191 (Shindo et al.), and 5,652,641 (Konishi)).

Other methods have been used to record the relative position of the first and fourth Purkinje images (the reflections from the anterior surface of the cornea and posterior surface of the crystalline lens, respectively). Their relative position is related to the direction of fixation of the eye (See, for example, U.S. Pat. Nos. 3,724,932 (Cornsweet et al.) and 4,729,652 (Effert)).

Electro-oculography has been used to record the direction of eye fixation by measuring weak electrical potentials on the skin that are related to eye position within the orbit (see, for example, U.S. Pat. No. 5,293,187 (Knapp et al.).

Search coils imbedded in scleral contact lenses have been used to record eye movements and eye position. The subject's entire head is positioned within a time-varying electromagnetic field. Depending on the angular position of the search coil within the electromagnetic field, more or less alternating current is induced in the coil as a measure of eye rotation (see, for example, Robinson D A, "A Method of Measuring Eye Movement Using a Scleral Search Coil in a Magnetic Field." IEEE Trans. Biomed. Electronics BME-10(4):137–145, 1963).

Each of the above techniques requires strict control of, or knowledge of, head position to determine where the eye is actually looking, that is, to determine the point of fixation of the eye. Apparatus must be attached to the head, or the head must be clamped within a head support, to provide accurate results. Furthermore, because these techniques monitor the position of the globe itself, and not the actual visual axis or point of fixation, the signal obtained must be calibrated against known directions of fixation of the eye, or known points of fixation, before useful measurements can be obtained.

A useful variation of eye tracking via the position of the corneal light reflection with respect to the pupil has been still photography of both eyes while the subject is instructed to look at a fixation light at or near the center of the camera lens (see, for example, U.S. Pat. Nos. 4,586,796 (Molteno) and 4,989,968 (Freedman)). With such a "photoscreening" device, asymmetry between the two eyes in the position of the corneal light reflection with respect to the pupils is indicative of misalignment of the eyes, that is, the clinical abnormality termed strabismus. Such photoscreening devices which image the pupils, however, have to be positioned a critical distance away from the subject to achieve proper focus of the pupils. It is often difficult to achieve and maintain this critical focus when photoscreening a freely-moving infant.

Apparatus for detecting the direction of eye fixation has been described in U.S. Pat. No. 5,331,149 (Spitzer and Jacobsen) wherein an array of illuminated pixels is presented to the eye in question, and light reflected from the fundus of the eye is detected by an array of photodetectors in registration with the array of pixels. As described therein, light is maximally reflected back toward the original pixel from which it came only when the fovea is aligned with that pixel, identifying fixation of the eye in the direction of that pixel. This apparatus fails to take into account the fact that substantial reflection of light occurs in a non-specular manner from the fundus, not only from the fovea but also from most areas of the fundus. Thus, substantial light will be reflected back toward every illuminated pixel, and the particular pixel aligned with the fovea may not be distinguishable by this technique.

Techniques which effectively track or monitor the optical projection of fundus landmarks out from the eye afford a somewhat more direct measurement of fixation direction. For example, the external location of the blind spot (the optical projection of the optic disc) can be monitored by test spots of light, presented within the presumed blind spot area, to which the subject responds if seen. A negative response indicates proper location of the blind spot. The subject must be alert and reliable, however, and accurate determination of the direction of eye fixation, or point of fixation, requires a calibration procedure as well as knowledge of the position of the eye in space.

A scanning laser ophthalmoscope can be used to lock onto, and track, the position of the optic disc, or the position of a branch point of a major blood vessel, in the fundus (see, for example, U.S. Pat. No. 4,856,891 (Pfibsen et al.). The visual axis itself cannot be tracked in this way, because there are no prominent landmarks in the fovea. Calibration with known directions of eye fixation, or known points of fixation, must still be performed, therefore, and precise alignment between the instrument and the pupil of the eye must be maintained at all times.

Although there are no prominent visible landmarks in the fovea of the eye, polarization effects can potentially be used to identify the fovea, utilizing the birefringent properties of the nerve fibers in the retina. The array of nerve fibers converging from all parts of the retina to the optic nerve head is characteristically unique. Many retinal nerve fibers diverge from the fovea and curve around to converge to the optic nerve head. Within the central four or five degrees of visual field, in the fovea, other nerve fibers, called Henle fibers, are arranged precisely radially, similar to the spokes of a wagon wheel. Both the retinal nerve fibers and the Henle fibers are known to have "form" birefringence, with the optic axis of the birefringence parallel to the direction of the fiber (see U.S. Pat. No. 5,303,709 (Dreher et al.) and klein Brink H B, van Blokland G J, "Birefringence of the Human Foveal Area Assessed In Vivo with Mueller-Matrix Ellipsometry," J. Opt. Soc. Amer. A 5:49–57, 1988)).

Further, a poorly-characterized source of dichroism exists in the human fovea, presumably related to lutein pigment particles that are aligned along the Henle fibers and along the ends of the retinal nerve fibers closest to the fovea. Both the birefringence of the nerve fibers, over the entire retina, and the dichroism in the area of the fovea can produce polarization-related changes in light that is reflected from the fundus of the eye. For polarization-related changes to be produced by the birefringence of the nerve fibers alone, the light must initially be polarized. The dichroism in the area of the fovea, however, produces polarization-related changes even in light that is initially non-polarized. The polarization-related changes that are produced at any one point are dependent on the direction and thickness of the nerve fibers at that point, as well as dependent in the foveal area upon the amount of dichroic pigment that may be present, aligned along the nerve fibers.

Scanning laser ophthalmoscopes have been described which yield maps of polarization-related changes across areas of the fundus of the eye (see Plesch A, Klingbeil U, Bille J. Digital laser scanning fundus camera. Appi. Opt. 26(8):1480–1486, 1987, and U.S. Pat. No. 5,177,511 (Feuerstein et al.)). The characteristic polarization-related changes which occur in the foveal area, however, have never been used to monitor or track the direction of fixation of the eye.

Techniques have been devised for actually measuring the amount of optical retardation produced by the retinal nerve fibers at points across the fundus of the eye (see, for example, U.S. Pat. No. 5,303,709). This measure of retardation is directly proportional to the thickness of the nerve fiber layer. Because the nerve fiber layer becomes attenuated and often irregular in serious eye disease such as glaucoma and optic nerve atrophy, determination of nerve fiber layer thickness provides a method for detecting such diseases.

Measurement of retardation produced by the retinal nerve fiber layer is hampered by a much larger amount of retardation that is normally produced by the naturally-occurring form birefringence of the cornea of the eye. Separate measurement of the corneal birefringence can be made, whereby the retardation produced by the corneal birefringence can be mathematically factored out of the total retardation to yield the retardation due to the birefringence of the nerve fibers. An alternative technique to avoid the complications introduced by the corneal birefringence is to compensate optically for the corneal birefringence as described in U.S. Pat. No. 5,303,709, whereupon the amount of retardation produced by the retinal nerve fibers can be measured directly. Such optical compensation of the corneal birefringence is technically demanding, however, involving special measurement and feedback systems.

SUMMARY OF THE INVENTION

An object of the present invention is to assess the direction of fixation of an eye by detecting polarization-related changes occurring in light reflected from the fundus of the eye. Because the polarization-related changes that occur are a function of the orientation of the birefringent nerve fibers in the illuminated area of the retina, and because the nerve fibers are arrayed in a characteristic way from one portion of the retina to another, the polarization-related changes provide information regarding which portion of the retina is aligned with the source of the light. Specifically, because the nerve fibers arising from the central fovea are uniquely arrayed with radial symmetry, unique polarization-related changes occur when the illuminated area of the retina is centered on the fovea, providing direct confirmation that the direction of eye fixation is toward the center of the source of light. Through use of the present invention, the fixation of the eye (projection of the fovea) in the direction of the source of light can be detected directly, without having to infer the direction of eye fixation by the tracking of external ocular reflections or anatomic landmarks.

A further object of the present invention is to assess the direction of fixation of the eye without requiring stabilization of the subject's head, without requiring apparatus attached to the head, without requiring precise alignment of the apparatus with the eye, and without requiring the apparatus to be a precise distance from the subject's eye. Such relative freedom of alignment and testing distance is obtained in embodiments of the present invention by providing a beam of illumination that is relatively large, overfilling the eye's pupil, and by relying on the retroreflection property of the eye to return the light reflected by the fundus of the eye toward the original source of light. By making the detection system substantially optically conjugate to the original source of light, light returning from the fundus is automatically captured by the detection system.

The eye serves best as a retroreflector when the eye is accurately focused in the same plane as the source of light. In this case, an actual image of the source of light is formed on the retina, where much of the reflection from the ftndus takes place. Reflected light from this image is focused by the optics of the eye, via the principle of autoconjugacy, directly back toward the light source. The amount of light that is reflected by the fundus is small, about 1/10,000 to 1/1,000 of the light incident on the retina, but by the process of autoconjugate retroreflection, a large portion of this reflected light is focused directly back toward the source of light, and thus toward the detection system which is optically conjugate to the source of light, typically via a beam splitter. If the subject's eye is anywhere within the beam of incident light (non-critical alignment), and if the subject focuses his or her eye on the source of light (non-critical testing distance), or on any object in the same frontal plane as the source of light, light will be efficiently retroreflected to the detection system. The detection of polarization-related changes in the light may be used to assess the direction of fixation of the eye.

Because the fovea of the eye subtends a relatively small visual angle (about four to five degrees), and because the very central portion of the fovea (the foveola) subtends an even smaller visual angle, detection of the center of the fovea requires that polarization-related changes be detectable from small, clearly-defined areas of the fundus of the eye. That is, the resolution of the illumination/detection system must be relatively high. In order to detect polarization-rclated changes from light reflected from small areas of the fundus, either the light that illuminates the fundus must be confined to a small area of the fundus (typically accomplished by making the light source small and placing it substantially in the plane of fixation of the eye) or the detector must "observe" only a small area of the fundus (typically accomplished by making the detector small and placing it substantially in the plane of fixation of the eye). The present invention contemplates both.

In principle, if the light source illuminates a small portion of the fundus, the detector can be large and need not be substantially in the plane of fixation of the eye. The detector is placed substantially in line with the light source so that it receives the light retroreflected from the fundus. Likewise, if the detector is small and observes only a small portion of the fundus, the light source can be large and need not be substantially in the plane of fixation of the eye. The light source is substantially in line with the detector so that the light source illuminates the portion of the fundus that the detector observes.

Thus, it is only necessary that either the light source or the detector be substantially in the plane of fixation of the eye (conjugate to the fundus of the eye). This is typically accomplished by having the eye fixate on the light source itself or on a fixation mark that is in a plane conjugate either to the light source or to the detector. Detection of retroreflected light is usually most efficient, however, when both the light source and the detector are in the plane of fixation of the eye and conjugate to one another.

In a still further embodiment, the present invention further contemplates reducing the measurement interference from the birefringence of the cornea of the eye by using incident light having a polarization state that is substantially independent of meridional direction. This can be attained by using incident light which is substantially circularly polarized, is substantially non-polarized, or has a polarization orientation which scans through the various meridians. The polarization state of each of these forms of incident light is substantially independent of meridional direction.

In another embodiment, the present invention contemplates reducing the measurement interference from the birefringence of the cornea by detecting polarization-related changes in the reflected light that are substantially independent of the meridional orientation of the corneal birefringence. To attain this object, changes in the Stokes parameter $S_3$ of the reflected light are measured, with the changes in the Stokes parameter $S_3$ of the detected light being substantially independent of the orientation of the corneal birefringence. Alternatively, changes in at least two components of the polarization state of the reflected light are measured, most conveniently the Stokes parameters $S_1$ and $S_2$, such that mathematical combination of these parameters yields polarization-related changes that are substantially independent of the meridional orientation of the corneal birefringence. Alternatively, in the case of polarization-related changes in the retroreflected light being due to the dichroic effect of the lutein pigment in the vicinity of the fovea, changes in the overall intensity of the reflected light are measured, with such overall intensity changes being independent of the meridional orientation of the corneal birefringence.

In a still further embodiment of the present invention, a polarization-based method and apparatus to assess the direction of fixation of the eye is provided, using pattern recognition of polarization-related changes in light reflected from the fundus.

In yet a further embodiment the present invention provides a polarization-based method and apparatus to assess the direction of fixation of both eyes of an individual simultaneously so that the state of alignment or misalignment of the individual's eyes with each other can be determined. At least two fixation monitor optical systems are provided, one for each eye, with the two systems sharing a common fixation target so that the proper simultaneous alignment of the two eyes on the common fixation target can be assessed.

In another embodiment, the present invention provides a polarization-based method and apparatus to track the direction of fixation of an eye relative to an external scene, also referred to as a field of view, for the purpose of selecting an object in the external scene to be recorded, targeted, or otherwise acted upon. A CCD (charge-coupled device) array of polarization-sensitive photodetectors is provided optically conjugate to the external scene. Polarization-related changes in light reflected from the fundus of the eye are recorded by the CCD array, yielding a polarization-modulated image of the fundus of the eye. A typical hourglass figure (or two- or four-bladed propeller figure) in the polarization-modulated image identifies the projection of the fovea of the eye and the point of fixation of the eye in the conjugate external scene.

BRIEF DESCRIPTION OF THE DRAWINGS

FIG. 4a is a flow chart illustrating the basic method used by the eye fixation monitor.

FIG. 22 is a diagram of an embodiment of the present invention used in an eye-tracking/feedback configuration for the purpose of aiming an external camera.

FIG. 22a is a diagram of an alternative to the detection system of the apparatus in FIG. 22.

FIG. 23 is a representative external scene displayed on the viewing screen in the apparatus of FIG. 22.

FIG. 24 is an illustration of the infrared CCD camera image of the eye's fundus in the apparatus of FIG. 22, with the eye looking at the tree in the display of the external scene.

FIG. 25 is the displayed external scene from FIG. 23 after feedback from analysis of the image of FIG. 24 has been used to rotate the external camera to aim at the tree.

FIG. 26 is an illustration of the infrared CCD camera image of the eye's fundus in the apparatus of FIG. 22 after feedback from analysis of the image of FIG. 24 has been used to rotate the external camera to aim at the tree.

FIG. 27 is a diagram of an embodiment of the present invention yielding a display of an external scene with a superimposed image of the eye's fundus showing the point of foveal fixation in the scene.

FIG. 28 is an illustration of the display obtained by the apparatus of FIG. 27, showing the superimposed image of the eye's fundus.

FIG. 29 is a diagram of an alternative arrangement to that of FIG. 27, with the image of the external scene and the image of the eye's fundus obtained with different cameras.

FIG. 30 is an illustration of the display from the apparatus of FIG. 29 showing the image of the external scene with a superimposed crosshair showing the point of fixation of the eye.

DETAILED DESCRIPTION OF THE INVENTION

Figure 1:
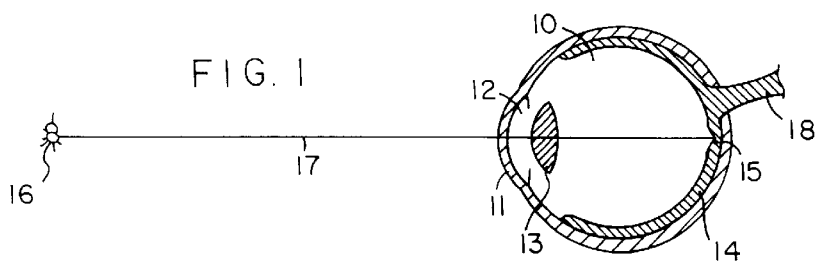
FIG. 1 is a cross section of a human eye identifying anatomical constituents as well as the axis of fixation.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The present invention contemplates providing a polarization-based assessment of the direction of fixation of the eye with minimum interference from the birefringence of the cornea. The amount and orientation of corneal birefringence vary from one eye to the next, but in any given eye the corneal birefringence is relatively constant in both amount and orientation in that portion of the cornea overlying the pupil of the eye. The corneal birefringence does change slightly with the angle of incidence of the incident light, but the polarization changes caused by this effect are small compared with the polarization-related changes occurring in the light reflected from one portion of the fundus versus another portion. Thus, by detecting the difference in the polarization-related changes that occur when the light is reflected from one portion of the fundus versus another portion of the fundus, a measurement of the fundus-induced polarization-related changes can be achieved that is relatively independent of the amount and orientation of the corneal birefringence in any given eye. In other words, the total amount of polarization-related changes in the light, to which the corneal birefringence contributes substantially, does not need to be measured or calculated. The differences in the total amount of polarization-related changes are sufficient to differentiate one portion of the fundus from another. For example, apparatus may be arranged to assess a single fundus area using autoconjugate retroreflection. The apparatus is calibrated by noting the polarization state that is detected by the apparatus while having the eye fixate in a desired direction. Any subsequent change in the polarization state will thereby indicate a change in fixation away from the desired direction. This technique is particularly effective when the apparatus is calibrated with the eye fixating directly on a small light source. In this case, the fundus area being assessed is the very center of the fovea, where there is no net direction to the nerve fibers. Any change of fixation away from the light source will move a bundle of roughly parallel nerve fibers into the illuminated fundus area, causing a change in the polarization state of the retroreflected light. This change thereby indicates a loss of fixation on the light source. Such a method of fixation monitoring is independent of the amount and orientation of corneal birefringence.

However, because the amount and orientation of corneal birefringence vary from one eye to the next, differences in the total amount of polarization-related changes, wlich represent the fundus-induced polarization-related changes, may be masked by particular orientations and magnitudes of the corneal birefringence unless the complete polarization state of the retroreflected light from the fundus is analyzed, a complicated analysis which may not be practical for many applications.

This can be understood with reference to the Poincaré sphere representation of the state of polarization, with Stokes parameters $S_1$, $S_2$, and $S_3$ serving as the mutually perpendicular Cartesian coordinate axes of the Poincaré sphere. If only Stokes parameter $S_1$ is monitored, for example, which is a practical method of detecting polarization changes, and if the orientation and magnitude of the corneal birefringence are such that the added polarization-related changes produced by the retinal birefringence occur in a direction which is substantially perpendicular to the SI axis, these retinal-birefringence-induced changes will not easily be detected. If, on the other hand, the orientation and magnitude of the corneal birefringence are such that the added polarization-related changes produced by the retinal birefringence occur in a direction which is substantially parallel with the $S_1$ axis, maximum retinalbirefringence-induced changes will be detected. Thus, because the orientation and magnitude of the corneal birefringence vary from one eye to the next, practical detection systems which monitor only one parameter of the polarization state will give non-uniform results from one eye to the next.

The present invention further provides a polarization-based method and apparatus for assessing the direction of fixation of the eye without prior calibration of the apparatus with one or more known directions of fixation of the eye. At least two areas of the fundus of the eye are assessed simultaneously or sequentially, and the polarization states of the light reflected from the different fundus areas are analyzed and compared. Two fundus areas producing an identical change in polarization state likely have equal thicknesses of nerve fibers oriented in the same direction. From the known visual angle separation of the fundus areas assessed, and from the known characteristic array of nerve fibers in the retina, the detection of equal polarization-related changes by one or more pairs of findus areas can identify with high probability a desired direction of eye fixation. As a specific example, if six fundus areas are assessed, at 2, 4, 6, 8, 10, and 12 o'clock on the perimeter of an imaginary circle subtending three degrees of visual angle on the fundus, the members of each opposing pair of retinal areas (the 6 and 12 o'clock areas, for example) will produce equal polarization-related changes only in two possible alignment positions, either when the six retinal areas are centered about the fovea, or when they are positioned within a uniform field of nerve fibers. In the former case, centered about the fovea, at least one of the pairs of equal polarization-related changes will be different from the others, whereas in the latter case, positioned within a uniform field of nerve fibers, the polarization-related changes of all six areas will be the same, distinguishing the two alignment position possibilities from one another. Alignment of the fovea with the center of the six retinal areas can thus be detected with high probability without the need for prior calibration of the apparatus with known directions of fixation of the eye.

The present invention further provides for assessing polarization-related changes during a scan of retinal areas, for example a scan in an annular pattern. A periodic signal is detected, representing the polarization-related changes occurring during the scan. The periodic signal, via the amplitudes and phases of its frequency components, represents a birefringence/dichroism signature of the particular annulus of retina scanned, as measured through the relatively constant birefringence of the cornea. This birefringence/dichroism signature can be used to identify various annular areas of the retina, and thus to assess the direction of fixation of the eye. For example, if the eye is fixating exactly in the center of a three degree annular scan, the nerve fibers radially arranged about the fovea will produce a birefringence/dichroism signal that has a strong frequency component exactly twice that of the scan frequency. If the eye is fixating on the rim of the annular scan, on the other hand, the birefringence/dichroism signature will have a strong frequency component exactly equal to the scan frequency and the phase of that frequency component can be used to identify the direction that the eye is fixating away from the center of the scan.

FIG. 1 illustrates the human eye 10. Light incident on the eye enters through the transparent cornea 11, passes through the pupil 12, traverses the transparent crystalline lens 13, proceeds toward the fundus, which is the inside aspect of the back of the eye, and strikes the retina 14 which lines the inner surface of the back of the eye. A central depression in the retina identifies the fovea 15 which is the area of the retina having the most acute vision. In viewing an object 16, the brain uses the neck and eye muscles to aim the eye at the object. The direction of fixation is defined by the orientation of the axis of fixation 17 which connects the object 16 with the fovea 15 of the eye. When the eye is fixed on the object 16, an image of the object 16 is formed on the fovea, and in conjugate manner an image of the fovea is projected onto the object 16. Further, retinal nerve fibers arising from all parts of the retina 14 travel along the surface of the retina and converge to form the optic nerve 18 which conveys visual information from the eye to the brain.

Figure 2:
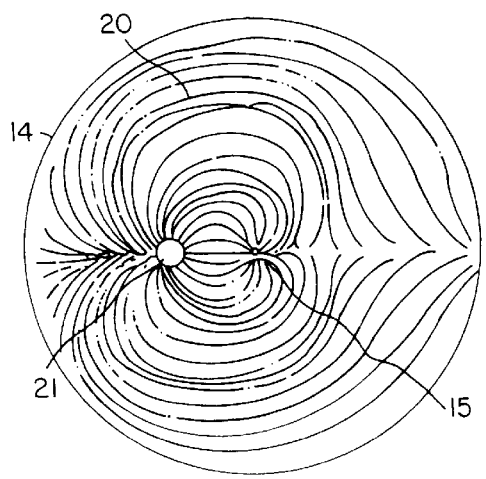
FIG. 2 is a plan view of the posterior retina of a human eye illustrating the characteristic array of nerve fibers.

FIG. 2 is a flat view of the posterior aspect of the retina 14, showing the characteristic array of retinal nerve fibers 20 arising from all parts of the retina and converging to the optic nerve head 21. A large fraction of the retinal nerve fibers arise from the foveal area where the concentration of neural elements is greatest and vision is most acute. As the retinal nerve fibers leave the foveal area, they first travel in a radial direction away from the fovea 15, then curve around as necessary to eventually reach the optic nerve head 21.

Figure 3:
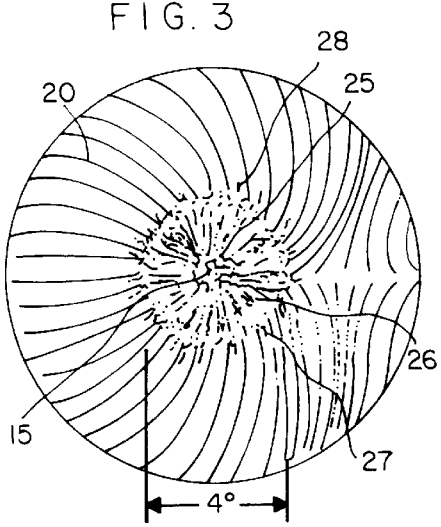
FIG. 3 is a plan view of the foveal area of a human eye illustrating the characteristic array of Henle fibers radiating from the center of the fovea.

FIG. 3 is an enlarged view of the foveal area of the retina, centered on the fovea 15, showing in greater detail the paths of the nerve fibers leaving the fovea. The cell bodies 25 of the photoreceptor elements are in the very center of the fovea. These cell bodies send nerve fibers 26 called axons to communicate with a ring of ganglion cells 27 surrounding the fovea. The ganglion cells in turn give rise to long axons of their own, constituting the retinal nerve fibers 20 which travel to the optic nerve to communicate with the brain.

The short axons 26 of the photoreceptor cell bodies are called Henle fibers and are arranged precisely radially about the center of the fovea 15. This precise radial array of Henle fibers 26, ending at the ring of ganglion cells 27, has an overall diameter subtending approximately four degrees of visual angle. Besides the area surrounding the fovea, the only other location in the retina having a radial array of nerve fibers is the area around the optic nerve head. The optic nerve head 21 subtends a visual angle of about five degrees. Therefore, an area of the retina at least six or seven degrees in diameter would have to be examined in order to detect the radial pattern of nerve fibers surrounding the optic nerve head. Thus, the array of Henle fibers 26 centered on the fovea 15, because of its relatively small angular size and its precise radial symmetry, constitutes a unique arrangement of nerve fibers within the retina and, therefore, can serve as a marker for the fovea. Identification of the location of the array of Henle fibers automatically identifies the location of the fovea, exactly centered in the array of Henle fibers.

Both the Henle fibers and the other retinal nerve fibers are birefringent, with the optic axis of the birefringence being parallel to the direction of the fiber. In general, this birefringence will change the state of polarization of polarized light that passes across the nerve fiber. Polarized light striking the retina, therefore, will be changed in its state of polarization as it passes through the layer of nerve fibers. A small fraction of the light passing through the nerve fibers is reflected by deeper layers of the fundus to pass back through the pupil of the eye. This portion of the light thus double-passes the nerve fibers, and its state of polarization is changed twice by the birefringence of the nerve fibers.

The state of polarization of light may be characterized by the ellipticity, the orientation of the major axis of the ellipse, and the handedness of the polarization. All of these parameters can be changed by the birefringence of the nerve fibers. The directions in which these parameters are changed, and the amounts, are functions of the orientation and the thickness of the layer of nerve fibers. Therefore, nerve fibers oriented in different directions will change the state of polarization differently.

A source of dichroism also exists in the human foveal area, from lutein pigment particles 28 which are aligned along the Henle fibers and along the ends of the retinal nerve fibers closest to the fovea. A dichroic material is birefringent but absorbs part of one of the polarization states of the doubly-refracted light, leading to a change in the state of polarization of the light passing through it. The dichroic pigment in the foveal area contributes to polarization changes in the light that passes through it. However, because the dichroic effect is aligned with the nerve fibers, the overall polarization changes that occur are still a function of the orientation of the nerve fibers. Both birefringence and dichroism can change the state of polarization of polarized light. However, birefringence has no net effect on non-polarized light. Dichroism, on the other hand, produces polarized light from non-polarized light by absorbing part of one of the polarization states of the doubly-refracted light. Therefore, if the retina is illuminated with non-polarized light, no polarization changes will occur anywhere in the retina, except in the foveal area. In this area the dichroism of the lutein pigment will produce polarized light having an orientation at each point that is dependent, at that point, on the orientation of the nerve fibers.

The cornea 11 of the eye also has birefringence; usually four or five times as much as the nerve fiber layers in the retina. In that portion of the cornea overlying the pupil, the corneal birefringence is relatively uniform in both amount and orientation. The corneal birefringence changes slightly with the angle of incidence of the incident light. However, the polarization changes caused by small changes in the angle of incidence are negligible compared to the polarization changes occurring in the light reflected from one portion of the fundus versus another portion.

Figure 4:
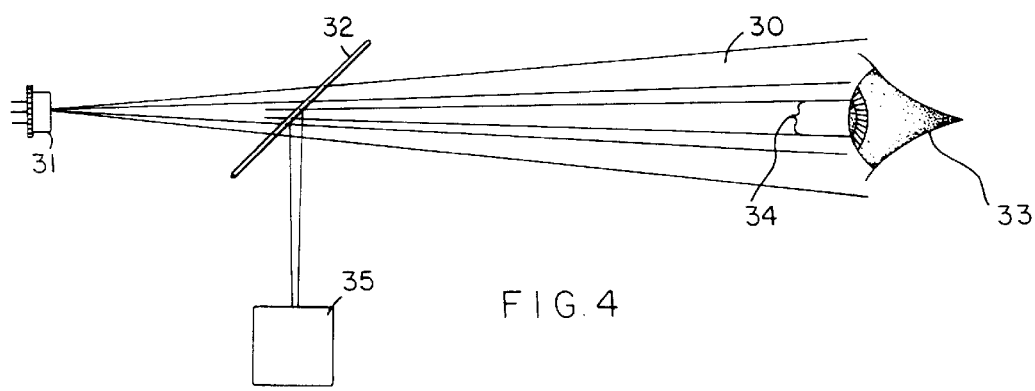
FIG. 4 is a diagram of a light source in combination with a polarization-sensitive detector arranged to detect light reflected from the fundus of an eye.

FIG. 4 illustrates a basic embodiment of the eye fixation monitor of the present invention. A beam of polarized light 30 from light source 31, (typically a laser diode), is directed through beam splitter 32 to be incident on eye 33, overfilling the pupil of eye 33 and easing alignment with the eye. Light 34, retroreflected from the fundus of eye 33 and focused by the optics of eye 33 back toward light source 31, is partially reflected by beam splitter 32 to fall upon a polarization-sensitive detector 35. Each direction of fixation of eye 33 will be associated with a particular difference in the polarization state of reflected light 34 as compared to incident light 30. Changes in this polarization state difference will be due primarily to the orientation of the nerve fibers in the portion of the retina illuminated by the incident light as fixation changes from one direction to another. Therefore, the stability of fixation is monitored by noting the stability in the polarization state detected by the polarization-sensitive detector 35.

Alternatively, the loss of fixation on a desired object may be detected by noting the polarization state of the light detected by detector 35 when the eye is known to be fixating on the desired object. Any change in the detected polarization state thereafter represents a loss of fixation on the intended object. This apparatus and method are particularly effective in detecting loss of fixation on the light source itself. With fixation on the light source, the area of the retina being illuminated is the center of the fovea, where there is no net direction to the nerve fibers. Any change of fixation away from the light source will move a bundle of roughly parallel nerve fibers into the illuminated fundus area, causing a perceptible change in the polarization state of the reflected light.

A flowchart of the basic method as detailed above is illustrated in FIG. 4a. The first step is generally to produce a beam of incident light and direct that beam of light toward the eye to illuminate the fundus (block 36). Next, light reflected by the fundus is isolated and detected (block 37). As a result, the incident light and the reflected light can be compared to determine polarization-related changes in the light caused by the eye (block 38). By correlating the polarization-related changes with changes known to occur with known fixation states of the eye, fixation state information on the eye is thus determined (block 39).

Figure 5:
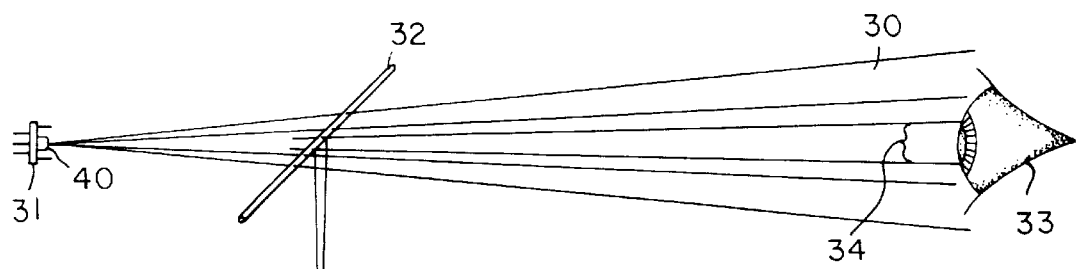
FIG. 5 is a diagram of a light source and detector which are located in conjugate planes with respect to each other via a beam splitter.

FIG. 5 shows the apparatus of FIG. 4 in which the light source 31 is shown in cross section, revealing emitter 40, and the polarization-sensitive detector 35 is represented by detector 41 having polarization-sensitive active surface area 42. The polarization sensitivity may be achieved, for example, by covering the photodetector with a thin linear polarizer. Furthermore, the emitter 40 and active surface area 42 are conjugate to one other via beam splitter 32. In other words, when viewed by eye 33 via beam splitter 32, the emitter 40 and active surface area 42 appear to be exactly superimposed on one another. This conjugate arrangement has the advantage of efficiently collecting the retroreflected light 34 from eye 33.

If eye 33 is focused upon emitter 40, or focused in the same frontal plane as emitter 40, a sharp, in-focus image of emitter 40 is formed on the retina of eye 33. The retroreflected light 34 from this tiny illuminated area on the retina of eye 33 will be imaged by eye 33 directly back toward the light source, emitter 40, because emitter 40 is conjugate to the retina of eye 33 via the optics of eye 33. Because active surface area 42 is conjugate to emitter 40 via beam splitter 32, the retroreflected light 34 being imaged back to emitter 40 will be partially reflected by beam splitter 32 directly to the center of active surface area 42. Whether eye 33 is in the center or periphery of incident light beam 30, the retroreflected light 34 from the retina of eye 33 will be imaged directly back to the center of active surface area 42. This relation which would not hold true if emitter 40 and active surface area 42 were not conjugate to one another via beam splitter 32. By making active surface area 42 larger than emitter 40, the retroreflected light 34 will be efficiently collected by detector 41 even if eye 33 is not focused exactly in the same frontal plane as emitter 40. If active surface area 42 were larger still, it would not even need to be substantially conjugate to emitter 40, via beam splitter 32, providing it is still roughly in alignment with emitter 40, so that it captures a substantial portion of the retroreflected light 34.

Figure 6:
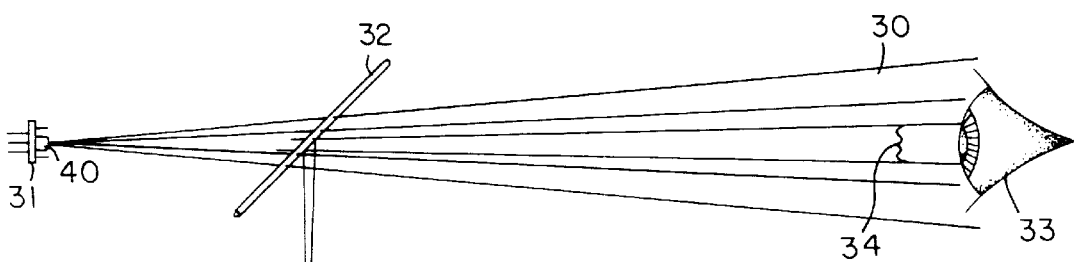
FIG. 6 is a diagram of a light source and detector which are conjugate with respect to each other, in size and in location, via a beam splitter.

FIG. 6 shows the apparatus of FIG. 5 with detector 41 replaced by polarization-sensitive detector 43 having active surface area 44. Active surface area 44 is relatively small and is precisely conjugate to emitter 40 via beam splitter 32. Active surface area 44 will collect the retroreflected light from eye 33 only if eye 33 is accurately focused in the frontal plane of emitter 40. The arrangement of FIG. 6 is thus sensitive to the focus of eye 33 as well as to the direction of fixation. Sensitivity to the state of focus of eye 33 is advantageous in some applications of eye fixation monitors.

Figure 6A:
FIG. 6a is a diagram of an alternative detector to the detector in FIG. 6, showing a bull's eye configuration.

FIG. 6a shows polarization-sensitive detector 45 as an alternative to detector 43 in FIG. 6. Detector 45 is a bull's eye detector, having a central active area 46 surrounded by an annular active area 47. These two active areas are connected electronically in a differential fashion, such that the output from the outside annular area is subtracted from the output from the central area. If the retroreflected light from eye 33 is well-focused in the center of detector 45, most of the light will strike the central active area 46, and a strong signal will be produced. If the retroreflected light is defocused, however, both the central and annular active areas, 46 and 47 respectively, will detect light, and the differential signal will be small. Such an arrangement increases the sensitivity of the detection system to defocus. The outputs of both active areas 46 and 47 may be summed for the detection of polarization-related changes in the retroreflected light.

Figure 7:
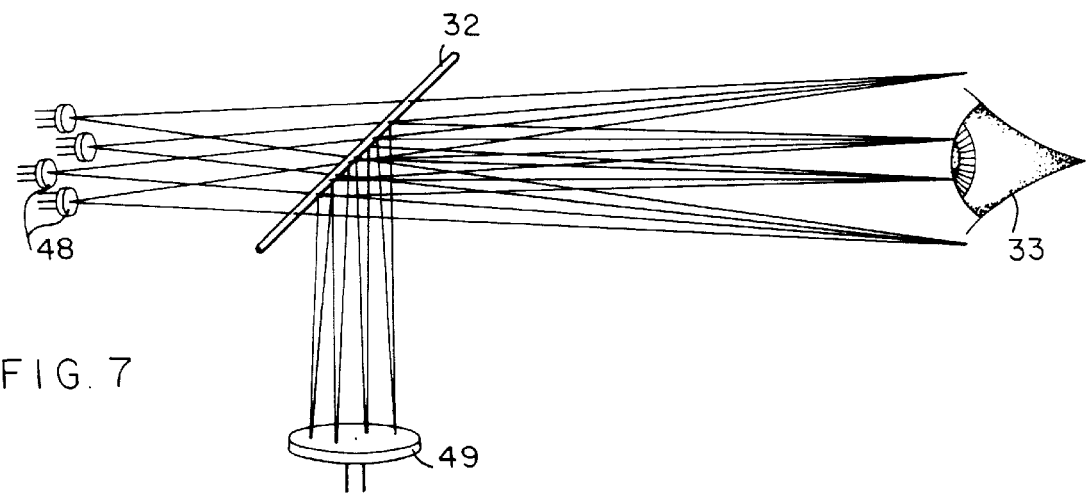
FIG. 7 is a diagram of an array of light sources which are substantially conjugate to a single large detector via a beam splitter.

FIG. 7 shows the apparatus of FIG. 4 with the single light source 31 replaced by an array of light sources 48, and with the polarization-sensitive detector 35 represented by a single large polarization-sensitive detector 49. The light sources 48 preferably are activated in sequence. Light retroreflected from eye 33 is detected by detector 49 for each respective light source 48. If detector 49 is substantially larger than the array of light sources 48, detector 49 need not be precisely optically conjugate to the array of light sources 48. The arrangement of FIG. 7 allows multiple retinal areas to be assessed sequentially for polarization-related changes in the retroreflected light. If any two retinal areas cause identical polarization-related changes, it is highly likely that the nerve fibers in those two areas have identical orientations. Such a finding can help determine which areas of the retina are aligned with the light sources, using a knowledge of the characteristic anatomic array of the nerve fibers in the retina.

Figure 8:
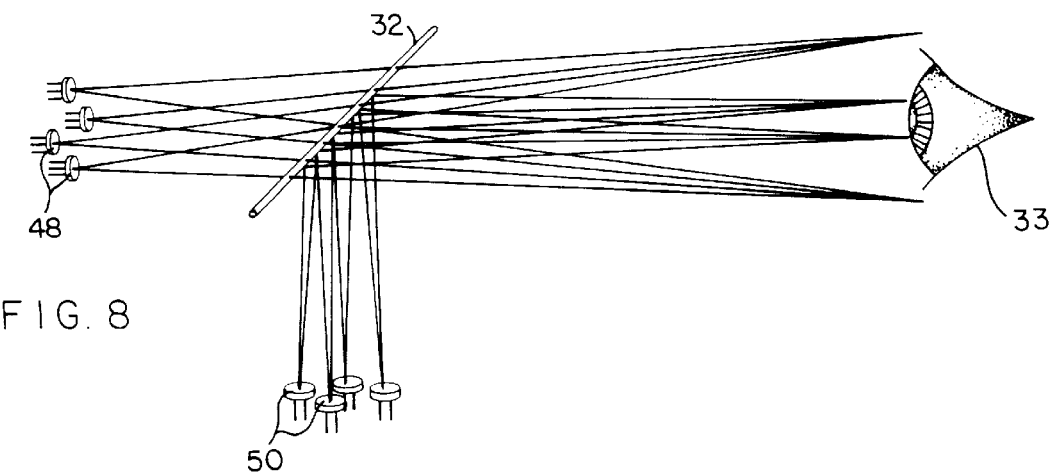
FIG. 8 is a diagram of an array of light sources wherein individual light sources are respectively conjugate to individual detectors in an array via a beam splitter.

FIG. 8 shows the apparatus of FIG. 7 with the single large polarization-sensitive detector 49 replaced by multiple polarization-sensitive detectors 50 corresponding to multiple light sources 48. Each detector 50 detects light from its respective light source 48 as retroreflected from eye 33. The preferred arrangement of FIG. 8 allows multiple retinal areas to be assessed simultaneously for polarization-related changes in the retroreflected light.

Figure 9:
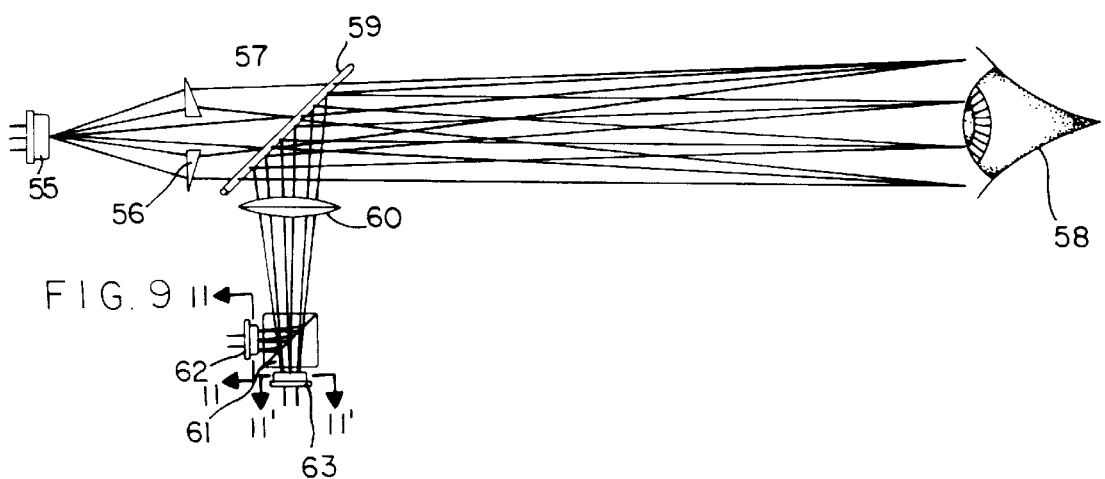
FIG. 9 is a diagram of a faceted prism which creates multiple effective light sources conjugate with respective portions of two six-element detectors.
Figure 10:
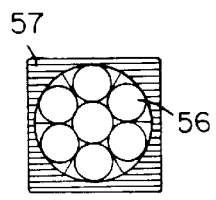
FIG. 10 is a diagram of a section taken through line 10—10 of FIG. 9, showing the various elements of the faceted prism.

FIG. 9 shows a preferred embodiment of the present invention wherein multiple light sources are created by a faceted prism, with six-element detectors used to provide multiple detectors. Light source 55 provides a diverging beam of polarized light incident on faceted prism 56 which has six base-in prism facets and a holed center as shown in sectional view in FIG. 10. Mask 57, containing seven round apertures, is placed adjacent to faceted prism 56 to isolate seven round beams of light. The outer six beams of light are refracted by the respective prism facets by the amount necessary for the peripheral beams to coincide with the center beam at the position of the eye 58, with all seven beams coincident at the eye and overfilling the pupil of the eye. The faceted prism produces six virtual images of light source 55, equally spaced around and separated (for example, approximately 1.5 degrees of visual angle) from the actual light source 55, all of which are viewed by eye 58 through beam splitter 59.

Figure 11:
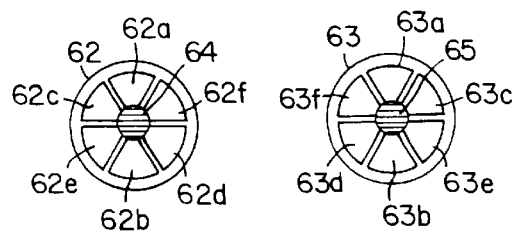
FIG. 11 comprises enlarged cross sections taken through lines 11—11 and 11'—11', of FIG. 9, showing the various elements of the two six-element detectors.

Light retroreflected from eye 58 in FIG. 9 is partially reflected by beam splitter 59 and is imaged by lens 60 onto the detection system including polarizing beam splitter 61 and six-element detectors 62 and 63. Six-element detectors 62 and 63, as shown in sectional view in FIG. 11, are aligned such that each pair of mirror-image detector segments, 62a and 63a, 62b and 63b, and so forth, are conjugate to each other via polarizing beam splitter 61, and also are conjugate via lens 60 and beam splitter 59 to the virtual images of light source 55 as formed by the faceted prism 56. The center areas of six-element detectors 62 and 63 are masked off by masks 64 and 65, respectively. The view of light source 55 as seen through the central aperture of faceted prism 56 is used only for fixation purposes by eye 58. The retroreflected light from the central light source does not need to be assessed or analyzed for polarization changes. The paired detector segments in FIG. 11, for example 62a and 63a, are electronically connected in differential fashion, allowing sensitive detection of polarization state.

The apparatus of FIG. 9 is used to assess polarization-related changes produced by six retinal areas simultaneously, constituting three pairs of opposing areas, with the members of each pair displaced about three degrees of visual angle from one another. This arrangement preferably detects fixation on the central light source. A unique combination of polarization-related changes is detected when the six retinal areas assessed are precisely centered about the fovea. In this position, the members of each pair of opposing retinal areas will show identical polarization-related changes, because the Henle fibers surrounding the fovea are oriented precisely radially. Areas of Henle fibers directly opposite the fovea from one another will be oriented identically. Each pair of opposing retinal areas will cause polarization-related changes that generally are different from those caused by the other pairs because the Henle fibers will be oriented differently for each pair of areas. Nowhere else in the retina will this combination of polarization-related changes be obtained for the six measuring spots. If the six illuminated areas fall on a patch of uniformly-oriented nerve fibers, the polarization-related changes in all six retinal areas will be identical. There will be no differences among the opposing pairs of identical polarization-related changes as is the case when centered on the radially-arranged Henle fibers. If centered on the optic nerve head, the six illuminated areas will show unpredictable and non-correlated polarization-related changes, because the optic nerve head subtends five degrees of visual angle, and the array of six illuminated areas subtends only three degrees of visual angle, not large enough to surround the optic nerve head.

It should be noted that the apparatus of FIG. 9, in detecting the eye's fixation on the central light source, functions with only minimum interference from the birefringence of the cornea. The total polarization-related change measured for each retinal area will be influenced by the corneal birefringence, but it is not the amount or type of polarization-related change that is of interest. It is the equality of the polarization-related changes in the three respective pairs of retinal areas assessed that is of interest. The orientation and amount of corneal birefringence are essentially constant for all of the retinal areas assessed. Therefore, the corneal birefringence will not interfere significantly with the necessary judgment of equality of polarization-related changes detected and will not interfere significantly with the detection of fixation on the central light source.

Figure 12:
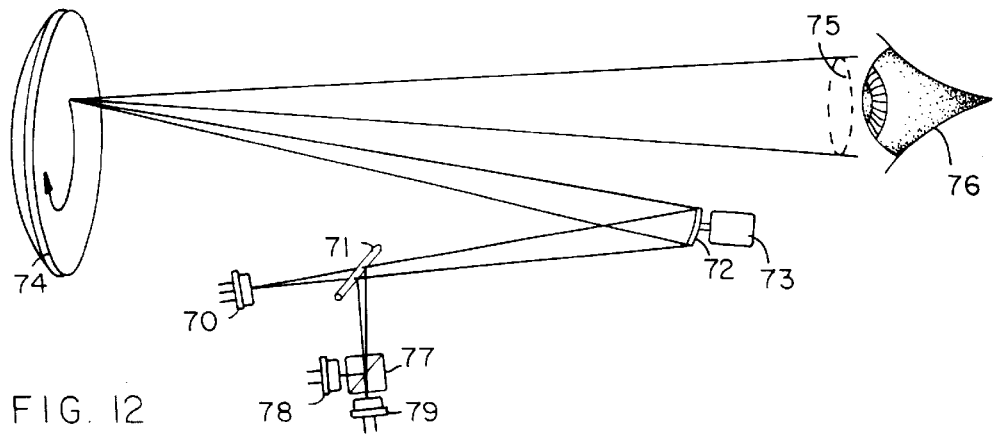
FIG. 12 is a diagram of an embodiment of the present invention using a light source wherein the light beam produced by the source is effectively scanned in a circle.

FIG. 12 shows another alternative embodiment of the present invention. A continuous scan of retinal areas is used to assess the direction of fixation of the eye. Light source 70 provides a diverging beam of polarized light which passes through beam splitter 71 and is incident on concave mirror 72. Concave mirror 72 is mounted in a tilted fashion on the shaft of motor 73 such that it wobbles slightly when the shaft rotates. Concave mirror 72 forms an image of light source 70 on the surface of a larger, stationary, concave mirror 74. As the shaft of motor 73 rotates, the image of light source 70 on the surface of concave mirror 74 is continuously scanned about a circular path. The curvature of stationary concave mirror 74 is chosen such that an image (dashed circle 75) of spinning concave mirror 72 is formed directly at the eye 76. All the light leaving spinning concave mirror 72 is imaged by stationary concave mirror 74 to pass through a stationary exit pupil of the apparatus, designated by dashed circle 75, which overfills the pupil of eye 76. Eye 76 sees the spinning image of light source 70 in the form of a circle of light on the surface of stationary concave mirror 74. A continuous annular scan of retinal areas is thus achieved by the light incident on the eye. The apparatus dimensions chosen provide an annular scan subtending about three degrees of visual angle.

Retroreflected light from eye 76 in FIG. 12 is reflected back toward the light source 70 by concave mirrors 74 and 72. Part of this light is further reflected by beam splitter 71 to the detection system including polarizing beam splitter 77 and photodetectors 78 and 79. Photodetectors 78 and 79 are conjugate to one another via polarizing beam splitter 77 and also are conjugate to light source 70 via beam splitter 71. The outputs of photodetectors 78 and 79 are electronically connected in differential fashion, allowing sensitive detection of polarization-related changes as the annulus of retinal areas is scanned.

Each orientation of nerve fibers in the retinal areas scanned with the apparatus of FIG. 12 will produce a different polarization-related change in the retroreflected light. A periodic signal is thus obtained with the apparatus of FIG. 12, representing the polarization-related changes occurring during repetitive scans. This periodic signal, via the amplitude and phase of its frequency components, represents a birefringence/dichroism signature of the particular annulus of retina scanned, as measured through the relatively constant birefringence of the cornea. This birefringence/dichroism signature can be used to identify various annular areas of the retina and thus used to assess the direction of fixation of the eye.

Figure 13:
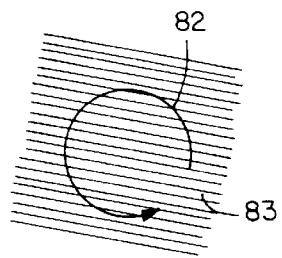
FIG. 13 is a diagram of a uniform patch of nerve fibers traversed by a circular scan of polarized light.
Figure 14:
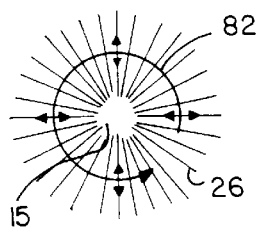
FIG. 14 is a diagram of the radially arranged nerve fibers in the fovea traversed by a circular scan of polarized light.

For example, in FIG. 13, if the three-degree-diameter annular scan 82 falls on a patch 83 of nerve fibers with uniform thickness and orientation, the periodic signal obtained will be relatively flat, showing no predominant frequency components. If, on the other hand, as shown in FIG. 14, the three-degree-diameter annular scan 82 is centered on the fovea 15, and thus falls entirely on the radial array of Henle fibers 26, a strong periodic signal will be obtained. Each orientation of the nerve fibers, from the horizontal to the vertical orientations which are indicated in FIG. 14, will be encountered twice during a 360 degree scan, so the periodic signal of polarization-related changes will be repeated twice during each 360 degree scan. In other words, if the scan is centered on the fovea, there will be a strong frequency component in the periodic signal of exactly twice the scanning frequency, identifying foveal fixation to be in the center of the circle of light.

Figure 15:
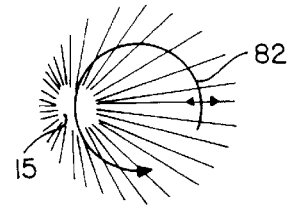
FIG. 15 is a diagram of the nerve fibers in the area of the fovea traversed by a circular scan of polarized light wherein one edge of the scan is passing through the center of the fovea.

Another illustrative example, shown in FIG. 15, shows the rim of annular scan 82 passing through fovea 15. Here the orientation of the scanned nerve fibers changes from horizontal to vertical (as indicated in FIG. 15) only once during each 360 degree scan. Therefore, there will be a strong frequency component in the detected signal that is exactly equal to the scanning frequency. This suggests fixation on or close to the rim of the circle of light.

Further information can be obtained from the phase of the detected signal with respect to the scan cycle. For example, if fixation is on the top of the circle of light, the detected periodic signal at the scan frequency will show approximately a 180 degree phase shift with respect to the signal obtained with fixation on the bottom of the circle of light. The phase of the signal, therefore, relative to the scan cycle, can be used, with calibration, to identify the direction that the eye is fixating away from the center of the circle of light. Such information can be used, for example, to drive a servo system, by methods well known to the art, to move physically, or move an image of, the conjugate source/detector unit to seek out the projection of the fovea of the eye, thereby finding the actual direction of fixation of the eye. By thus determining the direction of fixation of both eyes of a subject simultaneously, using a dual fixation tracking system, the alignment of the two eyes with one another can be determined, or the angle of misalignment can be measured.

Figure 16:
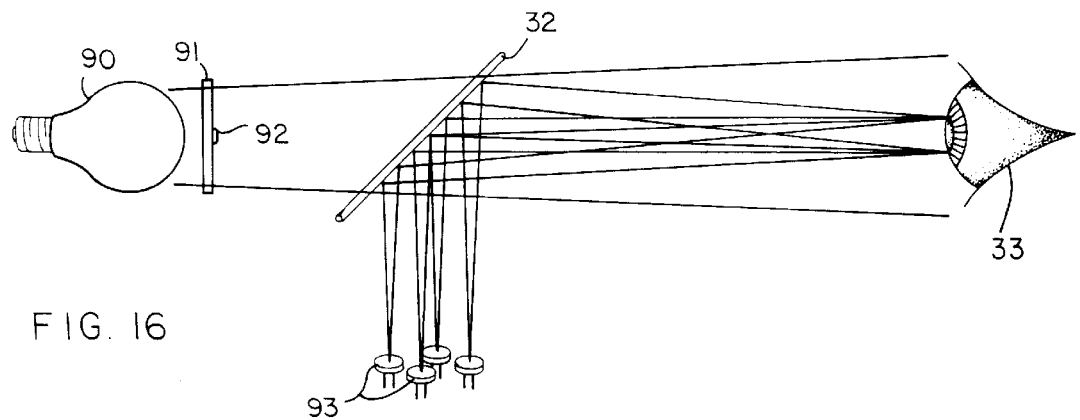
FIG. 16 is a diagram of an embodiment of the present invention using an extended light source and a fixation mark wherein the plane of the fixation mark is conjugate to an array of photodetectors via a beam splitter.

FIG. 16 shows the apparatus of FIG. 4 with light source 31 replaced by the combination of extended light source 90, polarizer 91, and fixation mark 92. Polarization-sensitive detector 35 has been replaced by multiple polarization-sensitive detectors 93. The polarization sensitivity is incorporated into the detectors, for example, by placing a thin polarizer over each photodetector surface. In this arrangement, extended light source 90 need not be precisely optically conjugate to multiple polarization-sensitive detectors 93. It is only necessary that the multiple polarization-sensitive detectors 93 be substantially optically conjugate to the retina of eye 33. This conjugacy is established by eye 33 fixating on fixation mark 92, which is conjugate via beam splitter 32 to the plane of multiple polarization-sensitive detectors 93. Retroreflected light from the large illuminated fundus area of eye 33 is partially reflected by beam splitter 32 to fall upon detectors 93. Each of the detectors 93 is thus responsive to light retroreflected from one retinal area, allowing the assessment of polarization-related changes from multiple retinal areas either sequentially or simultaneously. It should be recognized that this arrangement is the inverse of that shown in FIG. 7, with the differences being in the total amount of illumination of the retina and in the potential to assess multiple retinal areas simultaneously as well as sequentially. Detectors 93 may represent, for example, the individual elements of a CCD (charge-coupled device) array made polarization-sensitive by a superimposed polarizer. The thousands of such elements in the CCD array can yield a comprehensive map of polarization-related changes over an area of the retina, for the purpose of locating, and thus tracking, the characteristic polarization-related changes caused by the fovea. Such tracking applications will be described later in conjunction with FIGS. 22–32.

Figure 17:
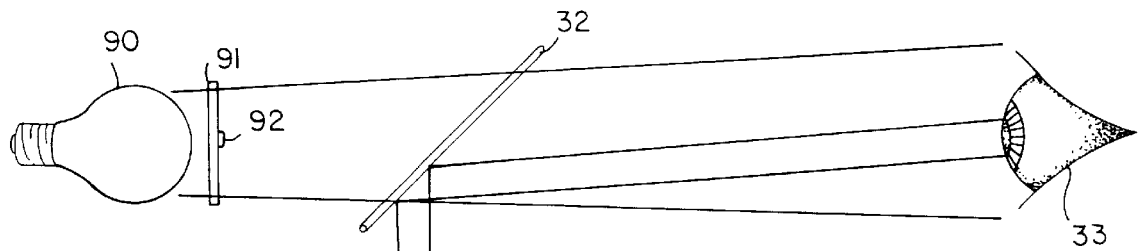
FIG. 17 is a diagram of an embodiment of the present invention using an extended light source and a fixation mark wherein the plane of the fixation mark is conjugate with a photodetector and a spinning mask is used to expose areas of the photodetector in a circular scan.

FIG. 17 shows the apparatus of FIG. 16 with the multiple detectors 93 replaced with a single large polarization-sensitive detector 94. Over detector 94, however, is a rotating mask 95 with a single, eccentric aperture 96. As the mask rotates, the area of the retina that is assessed for polarization-related changes is scanned in an annular pattern.

Whenever multiple areas of the retina are assessed simultaneously, information can be obtained regarding the direction of fixation of the eye from the pattern of polarization-related changes obtained. If multiple areas of the retina are assessed sequentially, information can be obtained regarding the direction of fixation of the eye from the pattern of the polarization-related changes obtained and also from the phase of the polarization-related changes obtained with respect to the assessment cycle.

Figure 18:
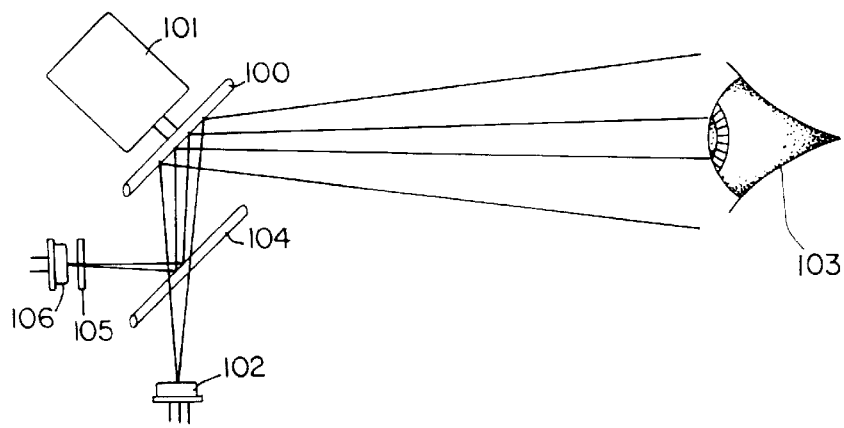
FIG. 18 is a diagram of an embodiment of the present invention with the detection system comprising a polarizing analyzer in combination with a photodetector.

FIG. 18 shows a basic embodiment of the present invention in which the areas of retina assessed are scanned in an elliptical fashion. Flat mirror 100 is mounted in a tilted fashion on the shaft of motor 101 such that it wobbles slightly when the shaft rotates. Diverging light from light source 102 is reflected by wobbling mirror 100 toward eye 103 such that the virtual image of light source 102 appears to eye 103 to move in an elliptical path, forming an ellipse of light. Retroreflected light from eye 103 is reflected by wobbling mirror 100 back toward light source 102 and is partially reflected by beam splitter 104 to be incident upon the polarization-sensitive detection system consisting of polarizer 105 and photodetector 106. This detection system will detect polarization-related changes in the retroreflected light from eye 103 as the image of light source 102 is scanned in an elliptical path on the retina, allowing an assessment of the direction of fixation of eye 103. Polarizer 105 and photodetector 106 constitute a simple polarimeter; that is, a device to measure at least one component of the state of polarization of incident light.

Figure 19:
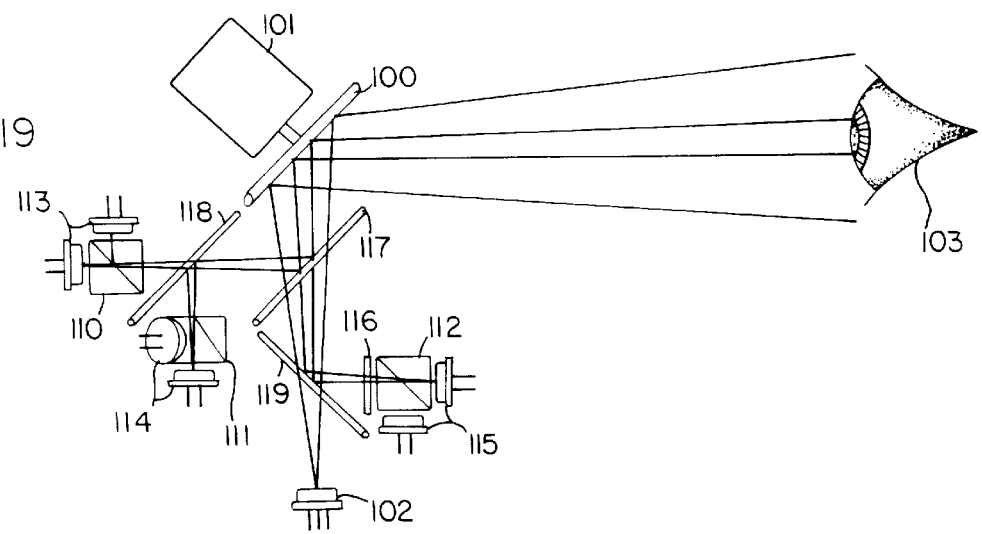
FIG. 19 is a diagram of an embodiment of the present invention with the detection system comprising an ellipsometer.

FIG. 19 shows the apparatus of FIG. 18 except that the detection system 105/106 has been replaced by a more complete detection system comprising polarizing beam splitters 110, 111, and 112, with associated photodetector pairs 113, 114, and 115, and quarter wave plate 116. Retroreflected light from eye 103 is partially reflected to polarizing beam splitters 110, 111, and 112 via beam splitters 117, 118, and 119. The photodetector pairs 113, 114, and 115 are each electronically connected in differential fashion, providing high sensitivity to subtle polarizationrelated changes. Polarizing beam splitter 111 is rotated forty-five degrees about the optical axis in comparison to polarizing beam splitters 110 and 112. Quarter wave plate 116 is positioned with its fast axis forty-five degrees from the polarization axes of polarizing beam splitter 112. With this detector system, Stokes parameters $S_1$, $S_2$, and $S_3$ of the polarized light retroreflected by eye 103 can all be measured simultaneously, completely characterizing the state of polarization. Paired detectors 113 measure Stokes parameter $S_1$, paired detectors 114 measure Stokes parameter $S_2$, and paired detectors 115 measure Stokes parameter $S_3$. A complete detection system such as this is usually called an ellipsometer. A detection system which provides a less-than-complete assessment of the state of polarization is termed a polarimeter, such as the simple detection system 105/106 in FIG. 18. Polarimeters are sufficient for proper operation for many forms of the eye fixation monitors which are the subject of the present invention.

Figure 20:
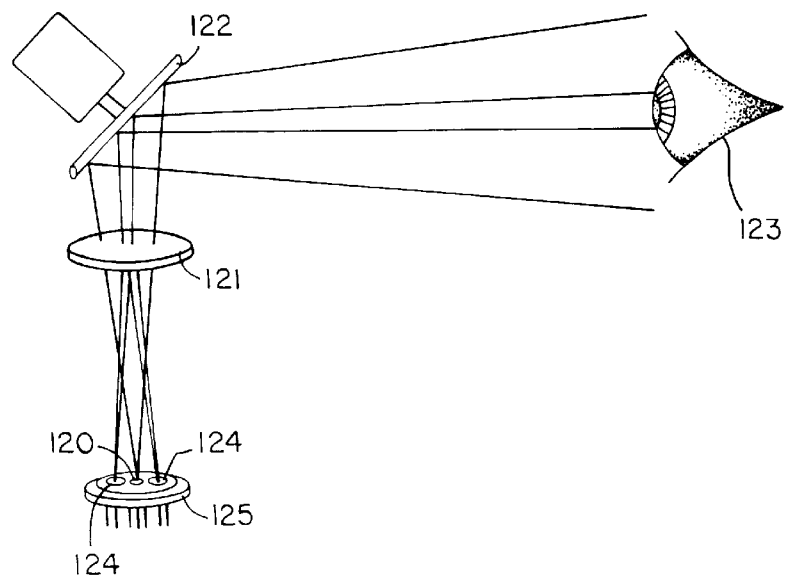
FIG. 20 is a diagram of an embodiment of the present invention using a holographic optical element to provide beam splitting and polarization analyzing functions.

FIG. 20 shows an embodiment of the present invention using a polarizing holographic optical element. Polarized light diverging from an emitter 120 passes through polarizing holographic optical element 121 to be reflected by wobbling mirror 122 toward eye 123. Retroreflected light from eye 123 is separated into orthogonally-polarized components by the polarizing holographic optical element 121 which also directs these respective components to two photodetectors 124 adjacent to emitter 120 in the integrated package 125. A polarizing holographic optical element can thus potentially replace the beam splitters in either or both the illumination and the detection pathways of most of the embodiments of the present invention.

Figure 21:
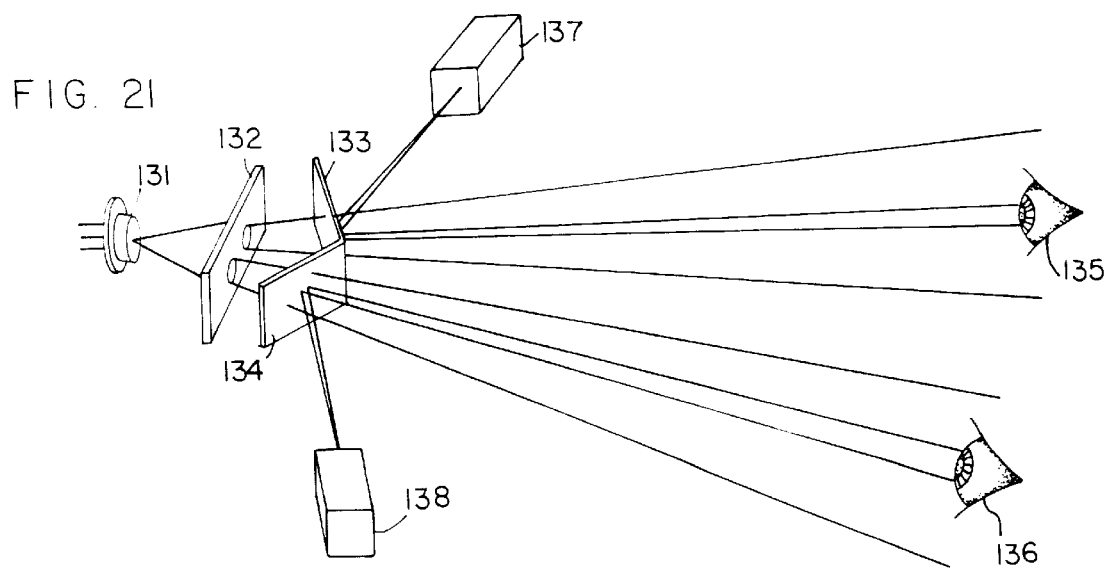
FIG. 21 is a diagram of two optical systems joined in a single instrument for the assessment of simultaneous fixation of both eyes of an individual.

FIG. 21 shows the joining of two optical systems in a single instrument for simultaneous monitoring of the alignment of both eyes of an individual. Diverging polarized light from light source 131 passes through two apertures in diaphragm 132 to continue through beam splitters 133 and 134 to overfill respectively the pupils of both eyes 135 and 136 of an individual. Retroreflected light bundles from eyes 135 and 136 respectively are partially reflected by beam splitters 133 and 134 to polarization-sensitive detection systems 137 and 138. Polarization-related changes in the retroreflected light bundles are used to assess the direction of fixation of both eyes 135 and 136 simultaneously, most conveniently detecting when both eyes 135 and 136 are simultaneously fixating on common light source 131, confirming normal alignment of eyes 135 and 136 with one another. Detection of only one eye fixating on light source 131, indicating that the other eye is misaligned with light source 131, is strongly suggestive of the abnormal condition known as strabismus, or misalignment of the eyes.

Instead of using common light source 131 in the joined optical systems of FIG. 21, two light sources may be used in conjunction with one or more mirrors that optically align the images of the two light sources with one another. An inverse arrangement to that in FIG. 21 is also possible, wherein two light sources are used, one directed to each eye, and a common polarization-sensitive detector is used, conjugate to both light sources via beam splitters. In this case, the two light sources are alternately energized or energized at different frequencies such that the signal obtained by the single polarization-sensitive detector can be decomposed into right and left eye components.

FIG. 22 shows an application of the apparatus of FIG. 16, in this case used in an eye-tracker/feedback configuration for the purpose of aiming an external camera. Extended light source 90 in FIG. 16 has been replaced by infrared laser diode 140 in FIG. 22. Diffuser 141 diffuses the infrared light output from laser diode 140, and condensing lens 142 gathers the diffused light and directs it to illuminate an area of the fundus of eye 145, passing first through polarizer 146 and being reflected by beam splitter 147 to eye 145. Retroreflected infrared light from the fundus of eye 145 passes through beam splitter 147. the light is reflected by hot mirror 148, and is focused by lens 149 through analyzing polarizer 150 onto CCD (charge-coupled device) image plate 151. The multiple-polarization-sensitive detectors 93 in FIG. 16 are replaced by analyzing polarizer 150 in combination with CCD image plate 151 in FIG. 22. CCD image plate 151 will thus receive an image of the fundus of eye 145, with polarization-related changes showing as areas of light or dark in the image. Polarizer 146 and analyzing polarizer 150 are each mounted to be rotatably adjustable about the optical axis by conventional mechanical means not shown so as to allow optimization of the contrast of the polarization-modulated image of the fundus of eye 145. Alternatively, polarizer 146 and analyzing polarizer 150 can be arranged to rotate continuously, in fixed relationship to each other, to provide a dynamically-changing polarization-modulated image of the fundus of eye 145, helpful in identifying features in the polarization-modulated image.

External video camera 153 is affixed to tilt/pan mount 154 such that video camera 153 can be aimed vertically and horizontally by electronic control. An image of the external scene 155 (the term "external scene" herein refers to and encompasses an external scene, an image of an external scene, a locus of points that are optically conjugate to an external scene, and a field of view) is captured by video camera 153 and is shown on display 156, for example an LCD (liquid crystal device) display. Display 156 is mounted in fixed relationship to beam splitter 148 and CCD image plate 151 via rigid frame 157 shown in dashed outline schematic form. CCD image plate 151 is optically conjugate to display 156 via lens 149 and beam splitter 148, such that each point on CCD image plate 151 has a respective conjugate point on display 156.

FIG. 23 shows a representative external scene captured by external video camera 153 and displayed on display 156. Image 158 of tree 159 appears in the image of the external scene. Crosshair 160 is superimposed on the external scene image on display 156 and is either drawn on display 156 or electronically generated and displayed in the center of the camera's view and in the center of display 156.

FIG. 24 shows the polarization-modulated image of the fundus of eye 145 as formed on CCD image plate 151, viewed from the CCD image plate at sectional line 24—24 in FIG. 22. Prominent in this infrared image are a round dark spot 161 with radiating brushes, representing the projection of the optic disc and radiating nerve fibers onto CCD image plate 151, as well as the small hourglass FIG. 162 representing the projection of the fovea onto CCD image plate 151. Eye 145 is fixing, and continues to fix, on the tree image 158 on display 156, as shown in FIG. 23.

Conventional image processing, represented by box 165 in FIG. 22, is used to identify the center of small hourglass FIG. 162 in the polarization-modulated image in FIG. 24. The center of small hourglass FIG. 162, representing the point of fixation of eye 145, is initially aligned with tree image 158 in the displayed image of the conjugate external scene shown in FIG. 23. Video camera 153 is not initially aimed directly at tree 159. The aiming errors are represented by the horizontal and vertical distances between the center of small hourglass FIG. 162 in FIG. 24 and the center of crosshair 160 in FIG. 23. These error signals are calculated electronically by conventional means, represented by box 166 in FIG. 22, and serve as feedback signals to motor controllers 167. The horizontal and vertical motors in tilt/pan camera mount 154 are thus activated to rotate video camera 153 to reduce the error signals to zero. Once this has been accomplished, the tree image 158 in FIG. 23 will be aligned exactly with crosshair 160 as shown in FIG. 25. Also the center of small hourglass FIG. 162 in FIG. 24 will be aligned exactly with the center of CCD image plate 151 as shown in FIG. 26.

It can thus be appreciated that wherever eye 145 looks in the image of the external scene on display 156, video camera 153 will be re-aimed under feedback control to point directly in the corresponding direction in external scene 155. If eye 145 fixes on a particular object in the view on display 156, the view will appear to move such that the crosshair 160 in the center of display 156 will come to rest exactly on the object of fixation.

An alternative arrangement to the combination of analyzing polarizer 150 and CCD image plate 151 in FIG. 22 is shown in FIG. 22a. Two CCD image plates 151a and 151b are positioned conjugate to each other via polarizing beam splitter 168 and are also conjugate to display 156 via beam splitter 148. The outputs of CCD image plates 151a and 151b are digitally subtracted from one another, pixel-by-pixel, by conventional electronic means represented by box 169 in FIG. 22a. The resulting differential polarization-modulated image of the fundus of eye 145 has superior contrast to the image obtained by analyzing polarizer 150 and CCD image plate 151 in FIG. 22.

FIG. 27 shows viewing apparatus which yields a video image of an external scene. Superimposed on the image of the external scene is a polarization-modulated image of the fundus of the viewing eye. Thus, the point of the eye's fixation within the scene can be determined by the location of the typical hourglass figure representing the projection of the fovea onto the scene. Specifically, light from infrared laser diode 170 is diffused by diffuser 171. Condensing lens 172 gathers the diffused light and directs it to illuminate an area of the fundus of eye 173, passing first through polarizer 174 and being reflected by beam splitter 175 to eye 173. Retroreflected infrared light from the fundus of eye 173 passes through beam splitter 175, is reflected by hot mirror 176, and is focused by lens 177 through analyzing polarizer 178 onto CCD image plate 179. Polarizer 174 and analyzing polarizer 178 are each mounted to be rotatably adjustable about the optical axis by conventional mechanical means not shown so as to allow optimization of the contrast of the polarization-modulated image of the fundus of eye 173.

Hot mirror 176 is coated to provide partial reflection of visible light from the distant external scene 180, thus serving as a beam splitter for visible light. The reflected portion of the visible light from external scene 180 is imaged by lens 181 onto first surface mirror 182. The visible light is reflected by first surface mirror 182, is collimated by lens 181, passes in part through beam splitter 176, and is imaged by lens 177 through polarizing analyzer 178 onto CCD image plate 179. The reflection/transmission properties of hot mirror/beam splitter 176 are chosen, in conjunction with the usable aperture of lens 181, such that the intensity of the visible light from external scene 180 received by CCD image plate 179 is low enough that it does not mask the details of the infrared light image of the fundus of eye 173 which is also received by CCD image plate 179.

FIG. 28 shows the superimposed images received by CCD image plate 179 in FIG. 27, viewed from CCD image plate 179 at sectional line 28—28 in FIG. 27. The visible light external scene is represented by image 183 of tree 184. The polarization-modulated image of the fundus of eye 173 is represented by round dark spot 185 with radiating brushes, representing the projection of the optic disc and radiating nerve fibers onto CCD image plate 179, and by typical small hourglass FIG. 186 representing the projection of the fovea onto CCD image plate 179. As can be appreciated from the relative positions of the superimposed images in FIG. 28, eye 173 is fixing on an object to the right of tree 184.

The basic apparatus illustrated in FIG. 27 is designed for viewing distant external scenes. Closer scenes may be viewed by proper repositioning of the optical elements, but it is most convenient to view closer scenes preferably by adding auto-focusing optics to the front of the apparatus, as illustrated schematically by dashed rectangle 187. Auto-focusing camera lenses, with their associated electronics, are well known in the art. Here the auto-focusing optics would be designed to collimate the light from closer objects such that the collimated light would follow the same paths through the remainder of the viewing apparatus as when a distant scene is being viewed. The apparatus in FIG. 27 may be fixed to an external structure or preferably either hand-held or head-mounted. The advantage of hand holding or head mounting is that the user is free to move the head or body to view over a much wider area than if the apparatus is fixed to an external structure.

FIG. 29 shows the same viewing apparatus as in FIG. 27 except that first surface mirror 182 in FIG. 27 has been replaced by CCD image plate 190. An image of the external scene 180 is thus recorded directly by CCD image plate 190 rather than being reflected back through the apparatus as in FIG. 27. Also, infrared filter 191 has been added to the apparatus in FIG. 29 to block visible light from reaching the original CCD image plate 179 which is now used only to record the polarization-modulated image of the fundus of eye 173. External scene 180, the fundus of eye 173, and both of the CCD image plates 179 and 190 are all conjugate to one another in this apparatus. The images received by the two CCD image plates 179 and 190 are reversed with respect to one another, and one of the images must be electronically reversed right-to-left before the two images can be superimposed. Conventional image processing is used on the image received by CCD image plate 179 to identify the center of the hourglass figure representing the center of the projection of the fovea of eye 173 onto CCD image plate 179. The location of the point of fixation is then added to the image of the external scene as a single crosshair, as shown schematically by block 194, before the combined image is displayed on monitor 195.

FIG. 30 shows a typical display from the apparatus of FIG. 29. The external scene is represented by tree image 183. The point of fixation of eye 173 is represented by crosshair 196. As can be appreciated from the relative positions of tree image 183 and crosshair 196, eye 173 is fixing to the right of tree 184.

Figure 31:
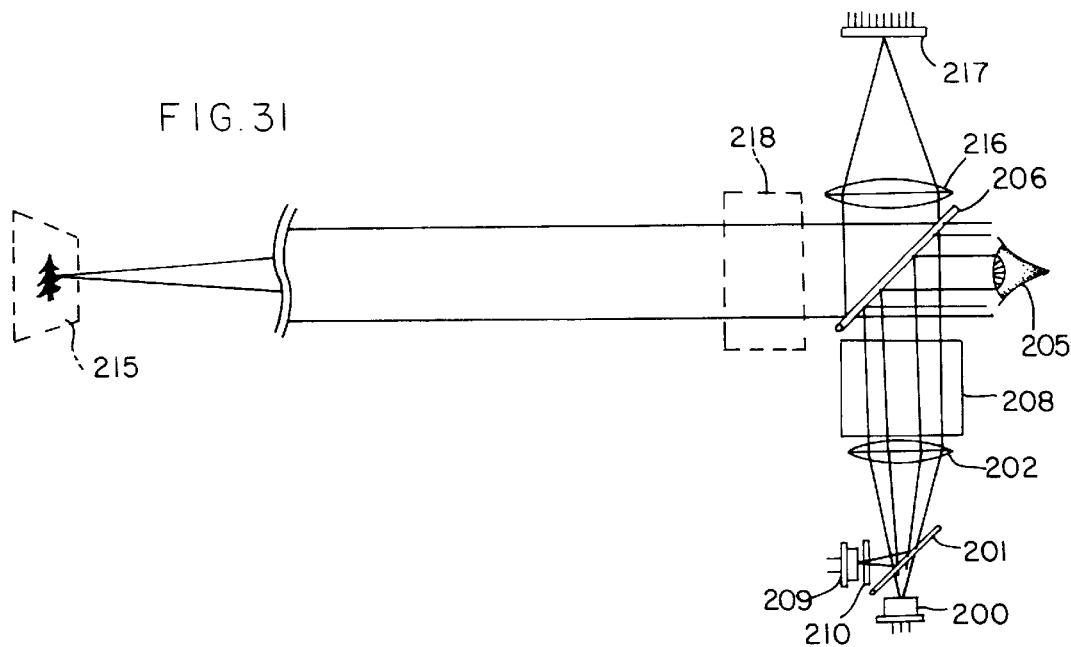
FIG. 31 is a diagram of an embodiment of the present invention wherein the eye's fundus is scanned by polarized infrared light in a raster pattern in registration with a video image taken of an external scene.

FIG. 31 shows a viewing apparatus that is similar to the apparatus of FIG. 29 except that a scanning system is used to obtain the infrared polarization-modulated image of the fundus of the viewing eye. This embodiment has the advantage of allowing a lower level of infrared illumination of the fundus of the eye. Specifically, infrared laser diode 200 provides linearly polarized infrared light which passes through beam splitter 201 and is collected by lens 202 to be directed toward eye 205 via hot mirror 206. Scanning system 208 is interposed between lens 202 and hot mirror 206. Schematically-shown scanning system 208 is one of many such systems that are well known to the art. Such systems typically use spinning polygon mirrors and various galvanometer-driven mirrors to scan a beam of light in a raster fashion. For example, such systems are used in scanning laser ophthalmoscopes, as in U.S. Pat. No. 5,268,711.

Retroreflected light from the fundus of eye 205 in FIG. 31 re-traces the illuminating light pathway, through scanning system 208 toward light source 200. Beam splitter 201 reflects a portion of this returning light to photodetector 209 which is rendered polarization-sensitive by placing analyzing polarizer 210 before it. A video image of the fundus of eye 205 is obtained from the signal from photodetector 209 by synchronizing the raster scan of a video monitor with the raster scan of scanning system 208. Laser diode 200 and analyzing polarizer 210 are each mounted to be rotatably adjustable about the optical axis, by conventional mechanical means not shown, for the purpose of optimizing the contrast of the polarization-modulated image that is obtained of the fundus of eye 205.

Visible light from the external scene 215 in FIG. 31 is reflected by hot mirror 206, which has been rendered partly reflective for visible light by proper coatings, to be imaged by lens 216 onto CCD image plate 217. Image plate 217 is thus conjugate to external scene 215 and to the plane of photodetector 209. The polarization-modulated image of the fundus of eye 205 is adjusted in size by proper choice and spacing of optical elements such that it is in conjugate registration with the CCD image plate 217. The typical small hourglass figure that identifies the projection of the fovea in the polarization-modulated image can then be correlated with the point of fixation of eye 205 on external scene 215.

For viewing of near objects using the apparatus of FIG. 31, auto-focus lens system 218 may be added to the front of the apparatus, shown schematically by a dashed rectangle, as was the case with the apparatus of FIG. 27.

Figure 32:
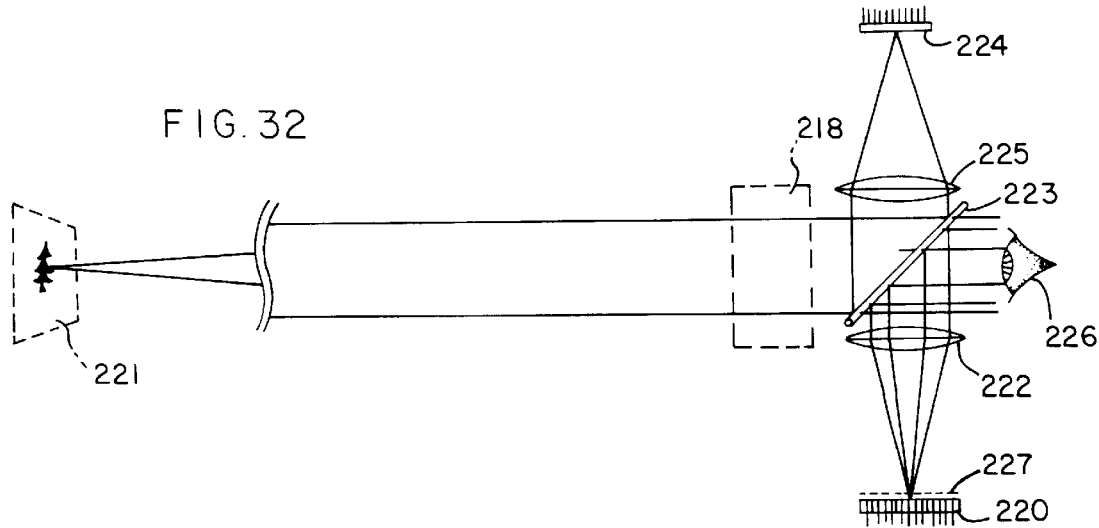
FIG. 32 is a diagram of an alternative arrangement to that in FIG. 31, wherein the scan of the eye's fundus and production of the polarization-modulated image of the eye's fundus are accomplished using an array of illuminated pixels in fixed combination with an array of photodetectors.

FIG. 32 shows a similar apparatus as in FIG. 31 except that the infrared illumination and detection systems have been replaced by a combination illumination/detection array that is conjugate with the external scene. Specifically, combination illumination/detection array 220 comprises a two-dimensional display array of infrared illumination pixels which may be energized in sequential or simultaneous fashion. Imbedded adjacent to, or surrounding, each illumination pixel is a photodetector, with the array of such photodetectors comprising a photodiode array or CCD array. Such combination illumination/detection arrays are described in U.S. Pat. No. 5,331,149.

The combination illumination/detection array 220 in FIG. 32 is optically conjugate to external scene 221 via lens 222 and hot mirror 223, as well as conjugate to CCD image plate 224. Infrared light from illuminated pixels in the combination illumination/detection array 220 is directed to eye 226 by lens 222 and hot mirror 223. Retroreflected light from the fundus of eye 226 is reflected by hot mirror 223 and is imaged by lens 222 onto combination illumination/detection array 220 where it is detected by the photodetector component of the combination illumination/detection array.

To obtain a polarization-modulated image of the fundus of eye 226 in FIG. 32, the light from the illuminating pixels in the combination illumination/detection array must be polarized, and an analyzing polarizer must be placed before each photodetector in the combination array. This is accomplished by a microarray of polarizers 227 placed over the combination illumination/detection array 220. Alternatively, a single sheet polarizer placed over the entire combination array can serve both polarizer and analyzer functions because of the nature of the polarization state changes that occur in the light retroreflected from the fundus of the eye.

In the polarization-modulated image obtained from the photodetector array component of the combination array 220 in FIG. 32, a typical small hourglass figure indicates the projection of the fovea of eye 226 onto the combination array 220. This identifies the point of fixation in external scene 221, which is conjugate to combination array 220 and is recorded by CCD image plate 224.

A potential obstacle in the implementation of the present invention lies in the fact that corneal birefringence varies in amount and orientation between eyes. Certain orientations and magnitudes of corneal birefringence may obstruct the measurement of differences in the amount of polarization-related changes in reflected light. Since the differences in the total amount of polarization-related changes represent the fundus-induced polarization-related changes, the complete polarization state of the retroreflected light from the fundus must be analyzed to provide consistently accurate results. To further illustrate this concept, FIGS. 33a–33d show typical changes in the polarization state of initially linearly polarized light that is incident on an eye, is retroreflected from the fundus of the eye, and emerges from the eye. The polarization state is specified by a point on the surface of a Poincaré sphere, which provides a three-dimensional graphical representation of all polarization states, whether linear, elliptical, or circular.

Figure 33C:
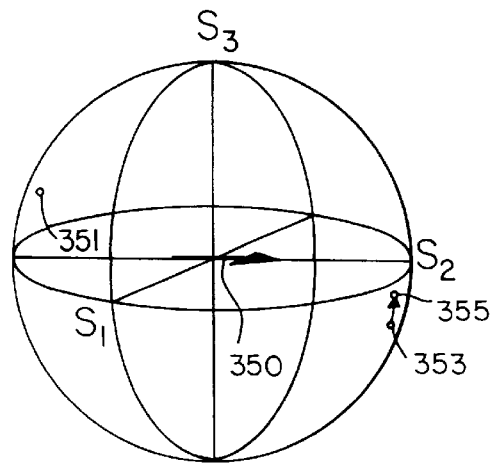
FIGS. 33a–33d are perspective views of the Poincaré sphere representation of the polarization state, showing sequential changes in the polarization state of incident linearly polarized light that passes through the cornea of an eye, passes through an area of retinal nerve fibers, is reflected from the fundus of the eye, passes back through the area of nerve fibers, and passes back through the cornea, exiting from the eye.
Figure 33A:
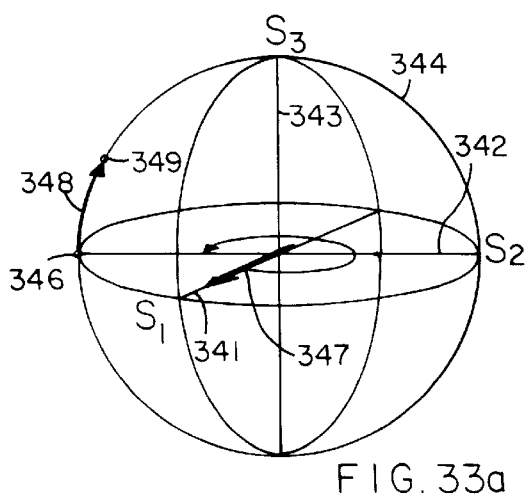

In FIG. 33a, mutually perpendicular axes 341, 342, and 343 represent the Stokes parameters $S_1$, $S_2$, and $S_3$ of the polarization state respectively, each of which can range from $-1$ to $+1$. The Poincaré sphere 344 has a radius equal to 1, so that for any point on the surface of the sphere, the square root of $(S_1^2+S_2^2+S_3^2)=1$. Each point on the surface of Poincaré sphere 344 represents a unique polarization state. The upper and lower poles of the sphere, where $S_3=1$ and $-1$ respectively, and $S_1$ and $S_2$ both equal zero, represent right-handed and left-handed circular polarization respectively. Any point on the perimeter of the equator of the sphere, in the $S_1/S_2$ horizontal plane, represents linear polarization. Points on the sphere between the equator and the poles represent elliptical polarization. The azimuth of the axis of linear polarization, or the azimuth of the major diameter of the ellipse of elliptical polarization, is indicated on the Poincaré sphere by a doubled angle measured counterclockwise from $S_1$ in the $S_1/S_2$ plane. If $+S_1$ represents a horizontal, zero-degree azimuth, then $+S_2$ represents 45 degrees, $-S_1$ represents 90 degrees, and so forth. For example, point 346 in FIG. 33a represents linear polarization with an azimuth of 135 degrees.

Passage of polarized light through a birefringent material changes the polarization state of the light. Both the cornea of the eye and the nerve fibers in the retina are birefringent, behaving as linear retarders, producing typical retardances of 30 degrees and 7 degrees respectively. A linear retarder can be represented within the Poincaré sphere as an eigenvector passing through the $S_1/S_2/S_3$ origin, lying in the $S_1/S_2$ plane, such as eigenvector 347 in FIG. 33a. If the retarder represented by eigenvector 347 produces a retardance of 30 degrees, the point on the sphere representing the polarization state rotates 30 degrees about the eigenvector, clockwise to an observer facing the head of the eigenvector. Thus, the polarization state 346 in FIG. 33a rotates 30 degrees about eigenvector 347, as indicated by arrow 348, to become polarization state 349. In other words, FIG. 33a can be used to illustrate the change in polarization state produced by passage of linearly polarized light into the eye through the cornea. The eigenvector of the corneal birefringence is at zero degrees, and the azimuth of the linear polarization state 346 is at 135 degrees. The retardance of the cornea is 30 degrees, and initial polarization state 346 is thus rotated to polarization state 349.

Figure 33D:
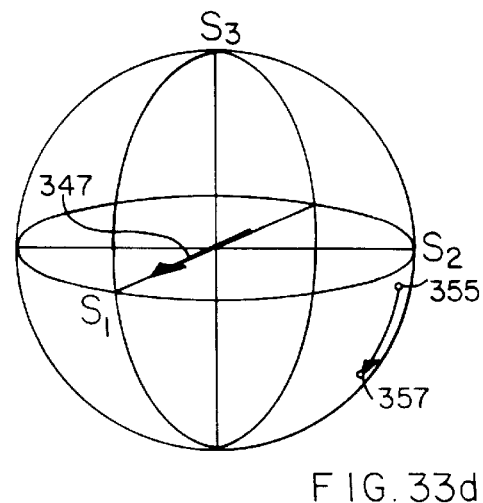
Figure 33B:
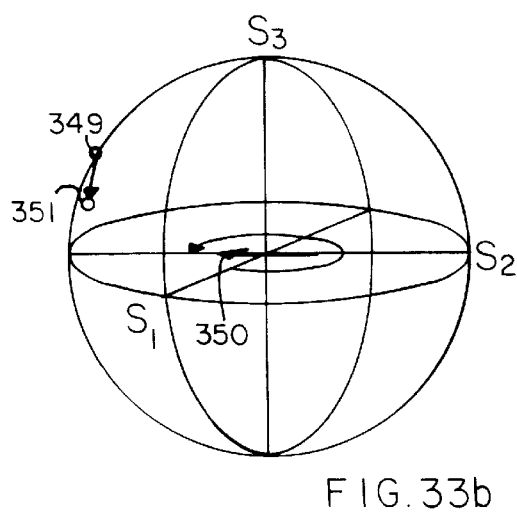

FIG. 33b illustrates the further change in polarization state that is produced by first passage of the light through a patch of retinal nerve fibers having a retardance of 7 degrees. The nerve fiber retardation is represented by eigenvector 350 oriented at 135 degrees (with this angle doubled to 270 degrees on the Poincaré sphere). The polarization state, beginning at point 349, rotates clockwise 7 degrees about eigenvector 350, moving to point 351.

FIG. 33c illustrates the further change in polarization state that is produced by reflection of the light by the layers of the fundus beyond the retinal nerve fibers, and by return passage through the nerve fibers. Reflection causes a change in polarization state from point 351 to 353 as well as a reversal of eigenvector 350, and return passage through the nerve fibers causes the polarization state to rotate clockwise about eigenvector 350 from point 353 to point 355.

FIG. 33d illustrates the further change in polarization state that is produced by passage of the light out of the eye through the cornea. The eigenvector 347 of the corneal birefringence is at zero degrees, producing a retardance of 30 degrees. The polarization state of the light thus rotates 30 degrees on the Poincaré sphere, clockwise about eigenvector 347, from point 355 to point 357.

As is evident from FIGS. 33a–33d, the final polarization state of linearly polarized light entering the eye, upon passing through the cornea and nerve fibers, being reflected from the fundus, and passing back through the nerve fibers and cornea, is strongly influenced by the corneal birefringence, which has an unknown but relatively large magnitude and an unknown orientation for a given eye.

In order to obtain information regarding the direction of fixation of the eye, one must be able to determine changes in the polarization state that are solely due to the retinal nerve fiber birefringence. Changes in the polarization state that are due to the retinal nerve fiber birefringence can conveniently be detected by slightly changing the direction of fixation, or, equivalently, slightly changing the direction of the measuring beam of light, such that the effects of one area of nerve fibers are compared with the effects of another area of nerve fibers. For small changes in angles of incidence, the birefringence of the cornea is substantially constant so that changes in the polarization state that occur between different directions of the measuring beam are due primarily to differences in the amount or orientation of the retinal nerve fiber birefringence from one retinal area to another.

The overall changes in the polarization state due to the retinal nerve fiber birefringence are small compared to the background changes in polarization state caused by the corneal birefringence, as illustrated in FIGS. 33a–33d. Also, for a given eye, with unknown magnitude and orientation of corneal birefringence, the location on the Poincaré sphere where retinal-nerve-fiber-induced changes must be detected is not generally predictable. For example, on the Poincaré sphere illustrated in FIG. 34, two potential changes in polarization state are illustrated, one change occurring from point 360 to point 361, and another change occurring from point 363 to point 364. It is desirable to be able to detect each of these changes, which can be seen to be nominally of equal magnitude, with uniform sensitivity. If only $S_1$ is measured in an attempt to detect changes in the polarization state, neither the 360 to 361 change nor the 363 to 364 change will be detected at all, because both of these changes occur perpendicular to the $S_1$ axis. If only $S_2$ is measured, the 360 to 361 change will be detected maximally because this change is parallel to the $S_2$ axis, but the 363 to 364 change will not be detected at all because this change is perpendicular to the $S_2$ axis. If only $S_3$ is measured, the 360 to 361 change will not be detected, but the 363 to 364 change will be detected maximally.

Figure 34:
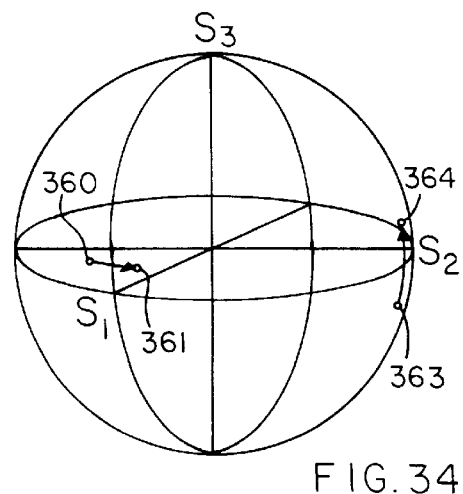
FIG. 34 is a perspective view of a Poincaré sphere showing representative changes in the polarization state of a beam of light traversing the retinal nerve fibers.
Figure 35:
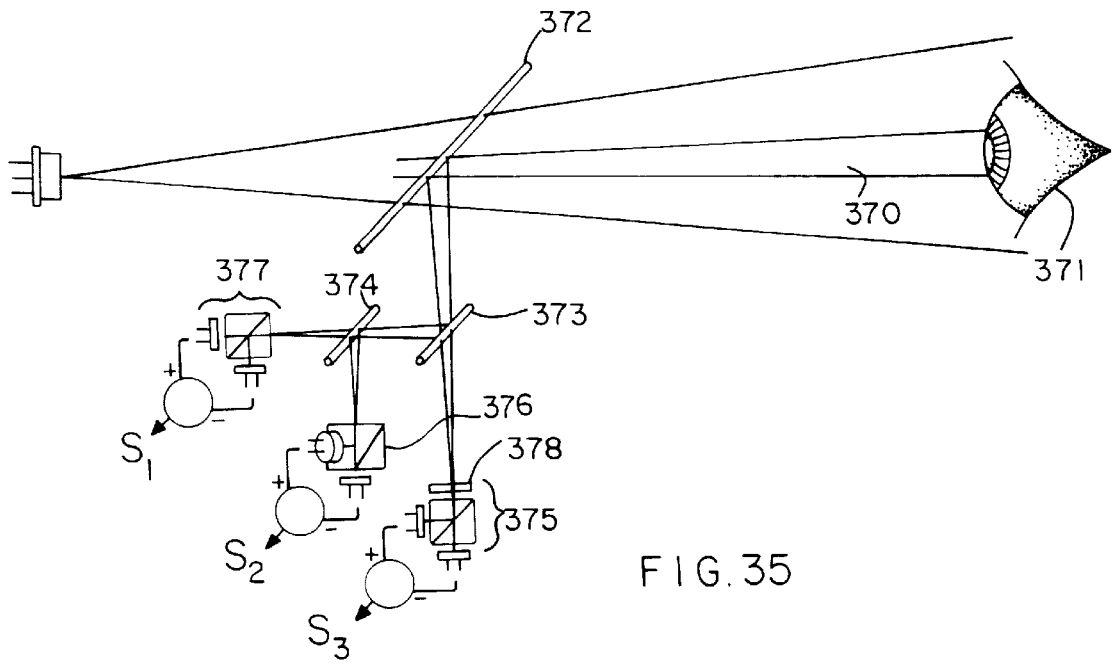
FIG. 35 is a diagram of a specific embodiment of the arrangement of FIG. 4, in which the polarization-sensitive detector of FIG. 4 comprises an ellipsometer.

As illustrated in FIG. 34, in order to be able to measure changes in polarization state at arbitrary locations on the Poincaré sphere, the complete polarization state of the light exiting the eye must be measured. For example, an ellipsometer as illustrated in FIG. 35 could be used to measure this complete polarization state. Light 370 exiting from eye 371 is partially reflected by non-polarizing beam splitters 372, 373, and 374 to be analyzed by differential polarization analyzers 375, 376, and 377. Each of differential polarization analyzers 375, 376, and 377 includes a polarizing beam splitter and two photodetectors, whose outputs are subtracted to yield values which are proportional to Stokes parameters $S_3$, $S_2$, and $S_1$ respectively. Differential polarization analyzer 375 also includes a quarter wave plate 378 to enable measurement of Stokes parameter $S_3$.

It is complicated to detect the retinal-nerve-fiber-induced changes in the polarization state by measuring the complete polarization state of the light exiting the eye. And yet, if the exiting light is analyzed by other means (for example, by measuring $S_1$, $S_2$, or $S_3$ alone, or by measuring the output of a photodetector behind a single polarizing analyzer), the result obtained will be very much dependent on the location on the Poincaré sphere where the retinal-nerve-fiber-induced changes in the polarization state are occurring. (See FIG. 34).

It is largely the unpredictable magnitude and orientation of the corneal birefringence which interferes with simplified measurement of retinal-nerve-fiber-induced changes in the polarization state of light retroreflected from the fundus of the eye. The particular magnitude and orientation of the corneal birefringence, along with the initial polarization state of the incident light, determine the location on the Poincaré sphere where retinal-nerve-fiber-induced changes in the polarization state must be detected. In order to simplify the detection of retinal-nerve-fiber-induced changes in the polarization state, it is desirable to be able to predict where on the Poincaré sphere these changes will occur, thereby reducing the interfering effects of the corneal birefringence on this detection. Such improvement in prediction can be obtained by using incident light having a polarization state which is substantially independent of meridional direction. For example, circularly polarized light may be used as the incident light.

Figure 36:
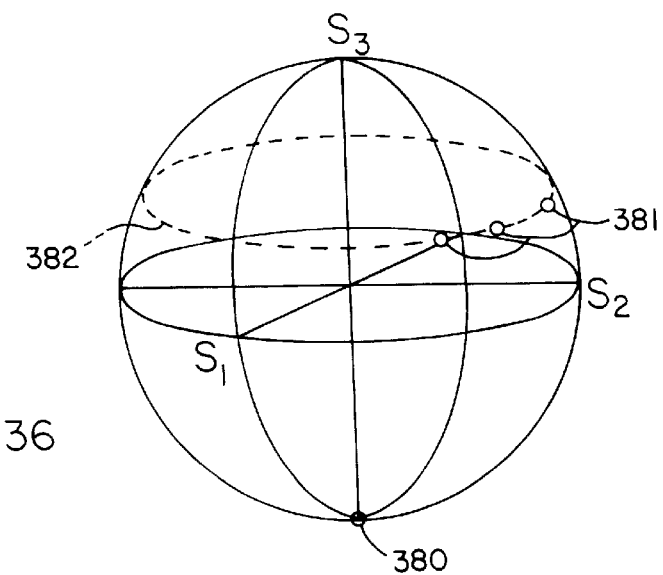
FIG. 36 is a Poincaré sphere showing representative final polarization states of circularly polarized light that has been acted upon only by the corneal birefringence in passing through the cornea, in being reflected from the fundus of the eye, and in passing out of the eye through the cornea.

FIG. 36 is a Poincaré sphere showing at point 380 the polarization state of incident light which is left-hand circularly polarized ($S_3=-1$). The birefringence of the cornea will have the effect of rotating the polarization state away from the inferior pole of the Poincaré sphere as the light double-passes the cornea, such that the final polarization state of the retroreflected light due to the corneal birefringence alone will be, for example, one of the points 381 along the latitude indicated by dashed line 382. The polarization states produced by the corneal birefringence alone can be predicted to be on a constant latitude of the Poincaré sphere, regardless of the orientation of the corneal birefringence. Perturbations of the polarization state away from this latitude can be interpreted as changes caused by the birefringence effects of the retinal nerve fibers, thus simplifying the detection of these changes.

Figure 37:
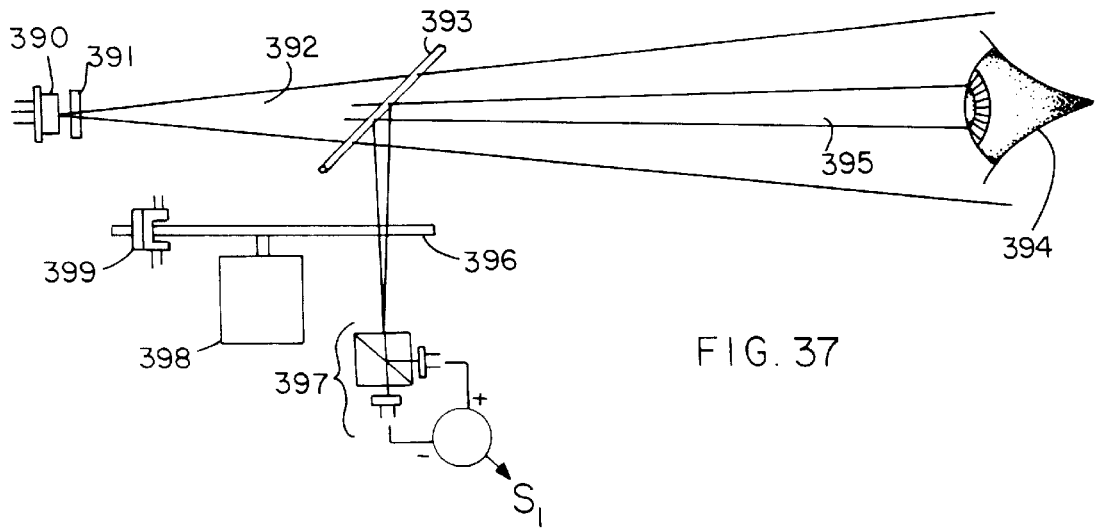
FIG. 37 is a diagram of an embodiment of the present invention wherein the incident light is circularly polarized.

FIG. 37 illustrates an embodiment of the present invention using circularly polarized light to detect retinal-nerve-fiber-induced changes in the polarization state of light retroreflected from the fundus of an eye. Laser diode 390, in combination with quarter wave plate 391, whose optic axis is 45 degrees to the meridian of polarization of laser diode 390, beams circularly polarized light 392 through non-polarizing beam splitter 393 toward eye 394. Light beam 395, which has been retroreflected from the fundus of eye 394, is partially reflected by non-polarizing beam splitter 393, passes through spinning half wave plate 396, and is detected by differential polarization analyzer 397. Differential polarization analyzer 397 includes a polarizing beam splitter and two photodetectors. The outputs of the two photodetectors are subtracted, yielding a value which is proportional to the Stokes parameter $S_1$ of the polarization state. Motor 398 spins half wave plate 396 at frequency Photoelectric detector 399, in combination with a small aperture in the rim of half wave plate 396, detects a synchronization pulse from spinning half wave plate 396.

Figure 38:
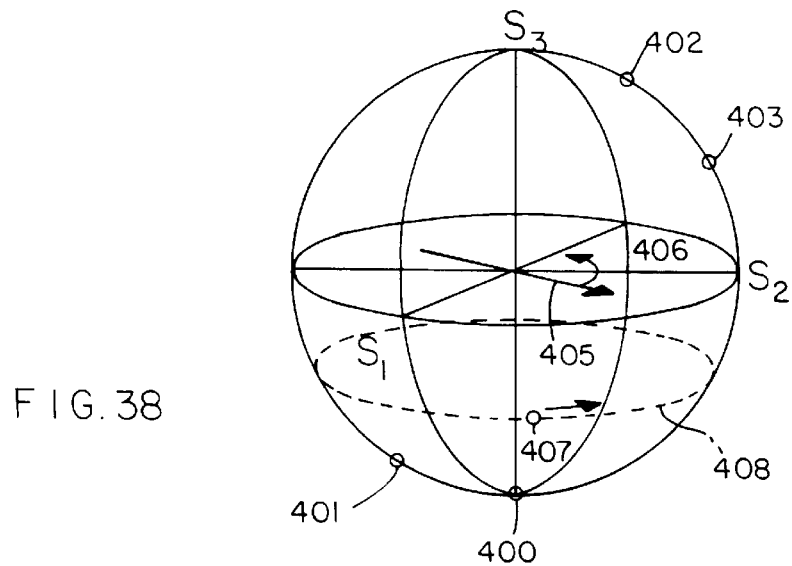
FIG. 38 is a Poincaré sphere showing representative initial and final polarization states of the light incident on the eye and retroreflected from the fundus of the eye using the apparatus in FIG. 37.

FIG. 38 shows a Poincaré sphere representation of the polarization state of light 392 in FIG. 37 as the polarization state is changed upon retroreflection from the fundus of eye 394 and passes through half wave plate 396. Point 400 represents the initial polarization state of light beam 392, left-hand circularly polarized, with $S_3=-1$. The corneal birefringence of eye 394 rotates the state of polarization upward approximately 30 degrees on the surface of the Poincaré sphere, for example to point 401. Ignoring the effects of the retinal nerve fibers for now, the light is reflected from the fundus, and upon reflection the polarization state jumps to the upper hemisphere of the Poincaré sphere, to point 402. Upon passing through the cornea to exit the eye as light beam 395, the light is further changed in its polarization state, with the state of polarization rotating approximately 30 degrees downward from point 402 to point 403.

As the reflected portion of light beam 395, at polarization state 403 in FIG. 38, passes through spinning half wave plate 396, it is further changed in its polarization state. The half wave plate 396 provides a retardance of 180 degrees, effectively rotating the polarization state by 180 degrees on the surface of the Poincaré sphere, about the fast axis 405 (eigenvector) of the half wave plate. The fast axis of the half wave plate spins about the $S_1/S_2/S_3$ origin in the $S_1/S_2$ plane in the direction of arrow 406. The polarization state of the light entering the half wave plate, initially at point 403, is thus rotated 180 degrees about fast axis 405, to point 407. As the fast axis of the half wave plate spins, the resulting polarization state traces out a circular path 408 on the lower hemisphere of the Poincaré sphere. This circular path is parallel to the equator and is equally far below the equator as point 403 is above the equator.

Path 408 in FIG. 38 represents the path that the polarization state will follow in the absence of effect from the retinal nerve fiber birefringence. Differential polarization analyzer 397 in FIG. 37, by measuring the Stokes parameter $S_1$, will yield a periodic signal whose peak-to-peak magnitude is a measure of the diameter of path 408 in FIG. 38. The meridional orientation of polarization state 403 is measured by the phase relationship of the periodic $S_1$ signal detected by differential polarization analyzer 397 with respect to the synchronization signal detected from spinning half wave plate 396 by photoelectric detector 399. Changes in the polarization state from point 403, caused by retinal nerve fiber birefringence, will be detected as a change in the amplitude of the periodic $S_1$ signal if the polarization state moves in latitude (up or down) on the Poincaré sphere, and as a change in the phase of the periodic $S_1$ signal if the polarization state moves longitudinally on the Poincaré sphere.

Figure 39:
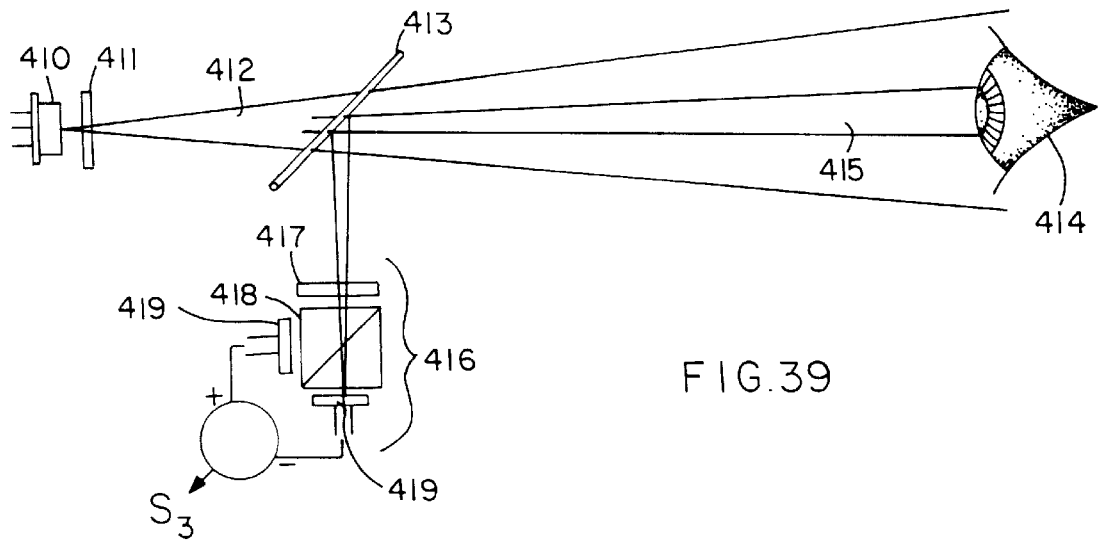
FIG. 39 is a diagram of an alternative embodiment of the present invention wherein the incident light is circularly polarized and the differential polarization analyzer measures the Stokes parameter $S_3$ of the polarization state.

The apparatus of FIG. 37 benefits from the use of circularly polarized light in reducing interference from the corneal birefringence in detecting retinal-nerve-fiber-induced changes in light retroreflected from the fundus of the eye. However, the measurement process is still complicated by the need for spinning half wave plate 396. FIG. 39 shows a preferred alternative apparatus which not only uses circularly polarized light but also uses a detection system which is independent of meridional orientation, further reducing interference from the birefringence of the cornea.

In FIG. 39, linearly polarized light from laser diode 410 is circularly polarized by quarter wave plate 411. Circularly polarized light beam 412 passes through non-polarizing beam splitter 413 toward eye 414. Light 415, retroreflected from the fundus of eye 414, is partially reflected by non-polarizing beam splitter 413 to be detected by differential polarization analyzer 416. Differential polarization analyzer 416 includes quarter wave plate 417, polarizing beam splitter 418, and two photodetectors 419. The outputs of the two photodetectors 419 are subtracted from one another. Because of the inclusion of quarter wave plate 417 in this differential polarization analyzer, the differential value obtained is proportional to the Stokes parameter $S_3$ of the polarization state.

Figure 40:
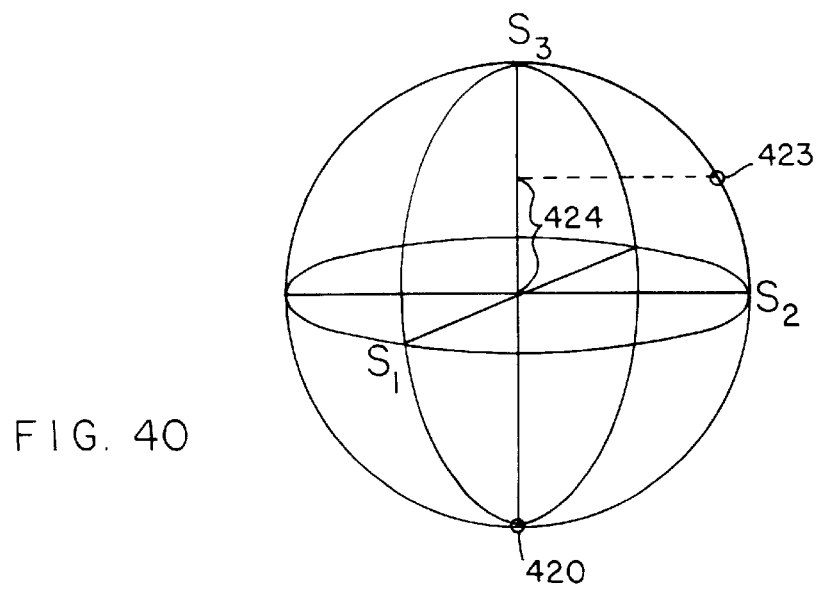
FIG. 40 is a Poincaré sphere showing representative initial and final polarization states of the light incident on the eye and retroreflected from the fundus of the eye using the apparatus in FIG. 39.

FIG. 40 shows a Poincaré sphere representation of the polarization state of light beam 412 in FIG. 39 as the polarization state is changed upon retroreflection from the fundus of eye 414. Point 420 represents the initial polarization state of light beam 412; left-hand circularly polarized, with $S_3=-1$. Point 423 represents the polarization state of light 415, exiting from the eye, after retroreflection from the fundus of the eye has taken place and the incident light 412 has double-passed the cornea. The effects of the retinal nerve fiber birefringence have been ignored in determining the polarization state produced only by the corneal birefringence and the retroreflection itself. Point 423 in FIG. 40 is similar to point 403 in FIG. 38.

The differential polarization analyzer 416 in FIG. 39 measures the Stokes parameter $S_3$ of the polarization state of light 415, corresponding to the distance 424 in FIG. 40. This distance is independent of the meridional orientation of the polarization state represented by point 423, and is, therefore, independent of the meridional orientation of the corneal birefringence. The Stokes parameter $S_3$ is a measure related to the ellipticity of the polarization state, with $S_3$=zero representing linearly polarized light, zero $<S_3<\pm1$ representing elliptically polarized light, and $S_3=\pm1$ representing circularly polarized light.

If the polarization state of light beam 415 changes, away from point 423, because of the effects of retinal nerve fiber birefringence, the change will be detected as a change in $S_3$ whenever the change away from point 423 has a vertical component on the Poincaré sphere. If one can be assured, therefore, that the retinal nerve fiber birefringence will change the ellipticity of the light passing through it, the apparatus of FIG. 39 can be used to detect the change in ellipticity, as measured by a change in the Stokes parameter $S_3$. The apparatus of FIG. 39, therefore, benefits not only from the use of circularly polarized light, but also from the measurement of polarization-related changes that are independent of meridional orientation. Thus, the retinal-nerve-fiber-induced changes in the polarization state of light retroreflected from the eye, as measured by this apparatus, are independent of the meridional orientation of the corneal birefringence.

Figure 41:
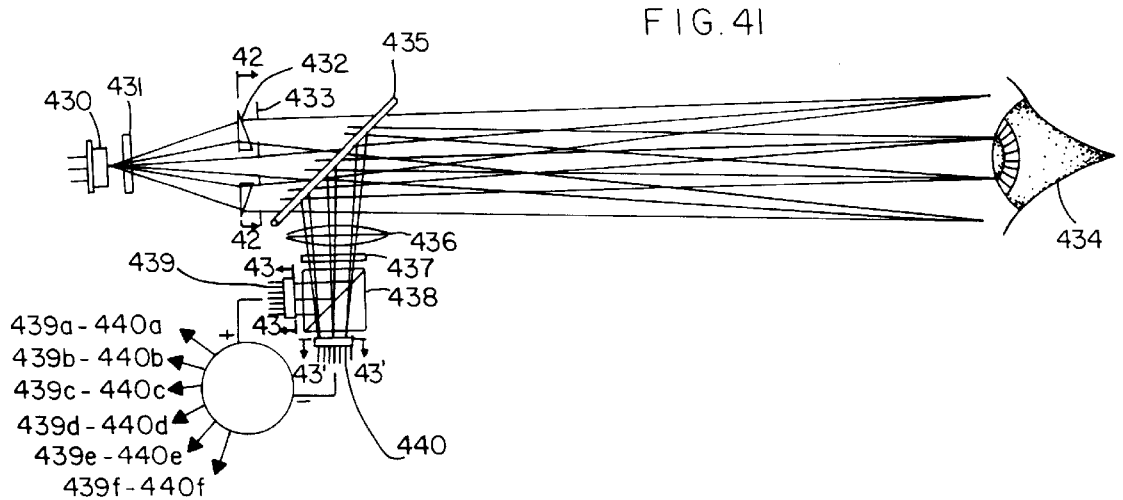
FIG. 41 is a diagram of a preferred embodiment of the present invention, incorporating a faceted prism and two six-element photodetectors, wherein the light incident on the eye is circularly polarized and polarization-related changes in the light retroreflected from the fundus of the eye are detected by measurement of the Stokes parameter $S_3$ of the reflected light.

FIG. 41 shows another preferred embodiment of the present invention which uses incident light with polarization state independent of meridional orientation and also detects polarization-related changes in the retroreflected light that are independent of the meridional orientation of the corneal birefringence. In FIG. 41, multiple light sources are created by a faceted prism, and six-element detectors are used to provide multiple detectors. Light source 430 provides a diverging beam of linearly polarized light. Quarter wave plate 431 converts the linearly polarized light to circularly polarized light which is incident on faceted prism 432. Faceted prism 432 has six base-in prism facets and a holed center as shown in sectional view in FIG. 42. Mask 433, containing seven round apertures, is placed adjacent to faceted prism 432 to isolate seven round beams of light, the outer six of which are refracted by the respective prism facets by the amount necessary for the peripheral beams to coincide with the center beam at the position of the eye 434, with all seven beams thus coincident at the eye and overfilling the pupil of the eye. The faceted prism thus produces six virtual images of light source 430, equally spaced around light source 430. The images are separated, for example, by approximately 1.5 degrees of visual angle from light source 430, and are viewed by eye 434 through beam splitter 435.

Figure 43:
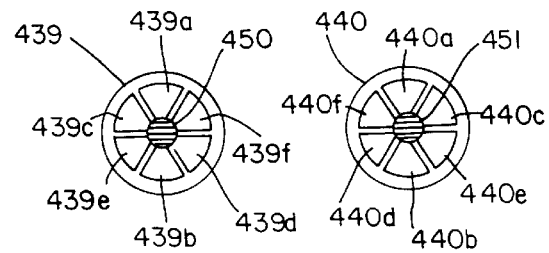
FIG. 43 comprises enlarged cross sections taken through lines 43—43 and 43'—43' of FIG. 41, showing the various elements of the two six-element detectors.

Light retroreflected from eye 434 in FIG. 41 is partially reflected by beam splitter 435 and imaged by lens 436 onto the detection system including quarter wave plate 437, polarizing beam splitter 438, and six-element detectors 439 and 440. Six-element detectors 439 and 440, as shown in sectional view in FIG. 43, are aligned such that each pair of mirror-image detector segments, 439a and 440a, 439b and 440b, and so forth, are conjugate to each other via polarizing beam splitter 438 and also are conjugate via lens 436 and beam splitter 435 to the virtual images of light source 430 as formed by faceted prism 432. As shown in FIG. 43, the center areas of six-element detectors 439 and 440 are masked off by masks 450 and 451, respectively. The view of light source 430 as seen through the central aperture of faceted prism 432 is used only for fixation purposes by eye 434. The retroreflected light from the central light source does not need to be assessed or analyzed for polarization changes. The paired detector segments in FIG. 43, for example 439a and 440a, are electronically connected in differential fashion, allowing sensitive detection of polarization state.

In the apparatus of FIG. 41, laser diode 430 and quarter wave plate 431 provide circularly polarized light incident on eye 434, with the polarization state of circularly polarized light being independent of meridional orientation. The use of quarter wave plate 437 in the differential polarization analyzer yields the measurement of Stokes parameter $S_3$ for each of the six detection channels, with that measurement thus being substantially independent of the meridional orientation of the corneal birefringence.

The apparatus of FIG. 41 is used to assess polarization-related changes produced by six retinal areas simultaneously, constituting three pairs of opposing areas, with the members of each pair displaced about three degrees of visual angle from one another. This arrangement is ideally suited to detect fixation on the central light source. A unique combination of polarization-related changes is detected when the six retinal areas assessed are precisely centered about the fovea. In this position, the members of each pair of opposing retinal areas will show identical polarization-related changes, because the Henle fibers surrounding the fovea are oriented precisely radially. Areas of Henle fibers directly opposite the fovea from one another will be oriented identically. However, each pair of opposing retinal areas will cause polarization-related changes that generally are different from those caused by the other pairs because the Henle fibers will be oriented differently for each pair of areas. Nowhere else in the retina will this combination of polarization-related changes be obtained for the six measuring spots. If the six illuminated areas fall on a patch of uniformly-oriented nerve fibers, the polarization-related changes in all six retinal areas will be identical, not showing differences among the opposing pairs of areas as is the case when centered on the radially-arranged Henle fibers.

If centered on the optic nerve head, the six illuminated areas will show unpredictable and non-correlated polarization-related changes, because the optic nerve head subtends five degrees of visual angle, and the array of six illuminated areas subtends only three degrees of visual angle. This is not large enough to surround the optic nerve head.

It should be noted that the apparatus of FIG. 41, in detecting the eye's fixation on the central light source, avoids significant interference from the birefringence of the cornea. The total polarization-related change measured for each retinal area will be influenced by the corneal birefringence. However, it is not the amount or type of polarization-related change that is of interest. It is the equality of the polarization-related changes in the three respective pairs of retinal areas assessed that is of interest. Because the orientation and amount of corneal birefringence are essentially constant for all of the retinal areas assessed, the corneal birefringence will not interfere significantly with the necessary judgment of equality of polarization-related changes detected. Therefore, such birefringence will not interfere significantly with the detection of fixation on the central light source.

Figure 44:
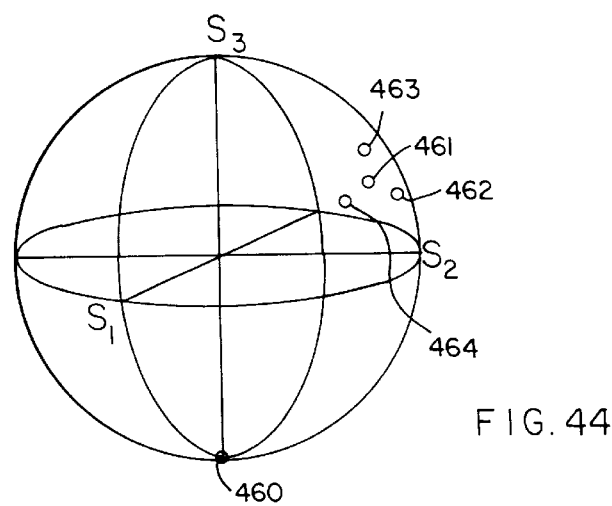
FIG. 44 is a Poincaré sphere showing representative initial and final polarization states of the light incident on the eye and retroreflected from the fundus of the eye using the apparatus in FIG. 41.

FIG. 44 shows a Poincaré sphere representation of the polarization states of the light in FIG. 41. The polarization states are changed by typical amounts upon retroreflection from the six areas of the fundus of eye 434. Point 460 represents the initial state of polarization of each of the light beams incident upon eye 434, left-hand circularly polarized, with $S_3=-1$. Point 461 represents an example of the state of polarization that each of these six beams of light retroreflected from the eye would have in the absence of retinal-nerve-fiber-induced polarization state changes. With the retinal nerve fiber birefringence acting, however, and with eye 434 fixating directly on light source 430 through the central aperture of faceted prism 432, point 462 represents the polarization states of one opposing pair of light beams exiting from the eye, and points 463 and 464 represent the polarization states respectively of the other two opposing pairs of light beams exiting from the eye. If eye 434 were not centrally fixating on light source 430, all six light beams retroreflected from the eye would generally have different polarization states from one another. It is precisely the fact that the two members of each pair of opposing light beams have the same polarization state, and the fact that the polarization state of at least one pair of light beams differs from the polarization state of the others, that identifies central fixation by eye 434. If retroreflected by a uniform of patch of nerve fibers, the members of each pair of opposing light beams would have the same polarization state, but no pair of light beams would have a different polarization state from that of the other pairs. This situation identifies a patch of uniform nerve fibers instead of identifying central fixation.

Figure 45:
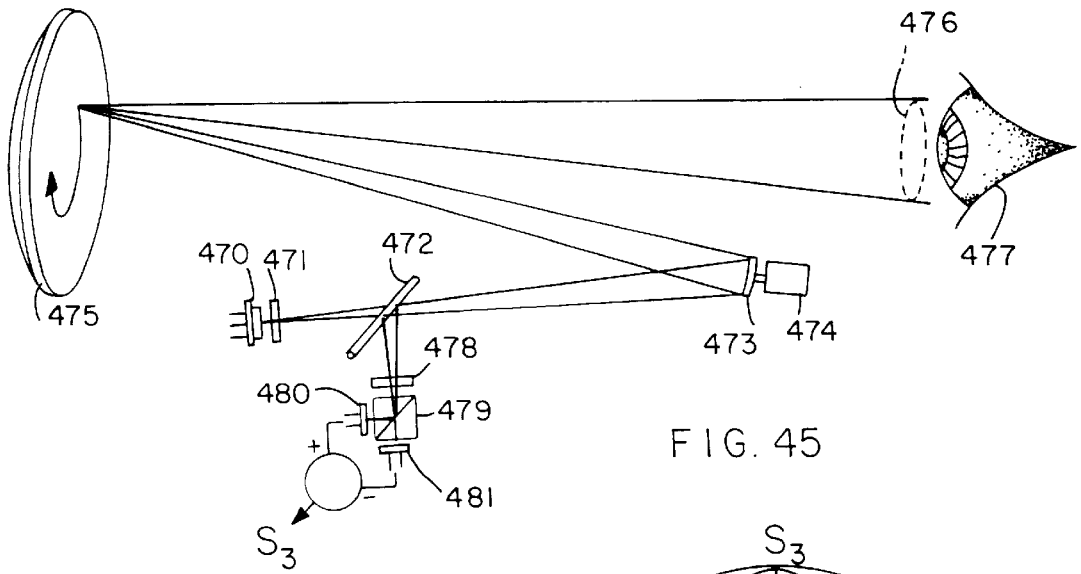
FIG. 45 is a diagram of an alternative embodiment of the present invention, incorporating a scanning mechanism which effectively scans the conjugate illumination/detection systems in a circle, wherein the light incident on the eye is circularly polarized and polarization-related changes in the light retroreflected from the fundus of the eye are detected by measurement of the Stokes parameter $S_3$ of the retroreflected light.

FIG. 45 shows an alternative embodiment of the present invention wherein a continuous scan of retinal areas is used to assess the direction of fixation of the eye. Light source 470 provides a diverging beam of linearly polarized light. Quarter wave plate 471 converts the linearly polarized light to circularly polarized light. The light continues through beam splitter 472 and is incident on concave mirror 473. Concave mirror 473 is mounted in a tilted fashion on the shaft of motor 474 such that it wobbles slightly when the shaft rotates. Concave mirror 473 forms an image of light source 470 on the surface of a larger, stationary, concave mirror 475. As the shaft of motor 474 rotates, the image of light source 470 on the surface of concave mirror 475 is continuously scanned about a circular path. The curvature of stationary concave mirror 475 is chosen such that an image (dashed circle 476) of spinning concave mirror 473 is formed directly at the eye 477. All the light leaving spinning concave mirror 473, therefore, is imaged by stationary concave mirror 475 to pass through a stationary exit pupil of the apparatus, designated by dashed circle 476, which overfills the pupil of eye 477. Eye 477 sees the spinning image of light source 470 in the form of a circle of light on the surface of stationary concave mirror 475. A continuous annular scan of retinal areas is thus achieved by the light incident on the eye, with the apparatus dimensions chosen to provide an annular scan subtending about three degrees of visual angle.

Retroreflected light from eye 477 in FIG. 45 is reflected back toward the light source 470 by concave mirrors 475 and 473. Part of this light is further reflected by beam splitter 472 to the detection system including quarter wave plate 478, polarizing beam splitter 479, and photodetectors 480 and 481. Photodetectors 480 and 481 are conjugate to one another via polarizing beam splitter 479 and also are conjugate to light source 470 via beam splitter 472. The outputs of photodetectors 480 and 481 are electronically connected in differential fashion, allowing sensitive detection of polarization-related changes as the annulus of retinal areas is scanned.

In the apparatus of FIG. 45, laser diode 470 and quarter wave plate 471 provide circularly polarized light incident on eye 477. The polarization state of circularly polarized light is independent of meridional orientation. Use of quarter wave plate 478 in the differential polarization analyzer yields the measurement of Stokes parameter $S_3$ for the retroreflected light from eye 477, with the measurement of Stokes parameter $S_3$ being substantially independent of the meridional orientation of the corneal birefringence.

Each orientation of nerve fibers in the retinal areas scanned with the apparatus of FIG. 45 will generally produce a different polarization-related change in the retroreflected light. A periodic signal is thus obtained with the apparatus of FIG. 45, representing the polarization changes occurring during repetitive scans. This periodic signal, via the amplitude and phase of its frequency components, represents a birefringence/dichroism signature of the particular annulus of retina scanned, as measured through the relatively constant birefringence of the cornea. This birefringence/dichroism signature can be used to identify various annular areas of the retina and therefore to assess the direction of fixation of the eye. For example, if the three-degree-diameter annular scan falls on a patch of nerve fibers with uniform thickness and orientation, the periodic signal obtained will be relatively flat, showing no predominant frequency components. If, on the other hand, the three-degree-diameter annular scan is centered on the fovea, and thus falls entirely on the radial array of Henle fibers, a strong periodic signal will be obtained. Each orientation of the nerve fibers will be encountered twice during a 360 degree scan, so the periodic signal of polarization-related changes will be repeated twice during each 360 degree scan. In other words, if the scan is centered on the fovea, there will be a strong frequency component in the periodic signal of $2\eta_s$, exactly twice the scanning frequency of $f_s$, identifying foveal fixation to be in the center of the circle of light.

Figure 46:
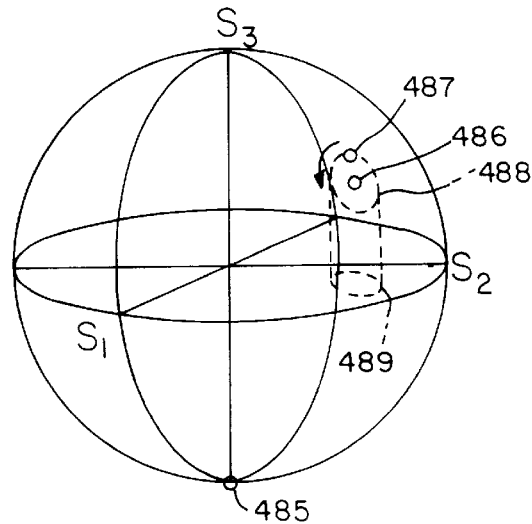
FIG. 46 is a Poincaré sphere showing representative initial and final polarization states of the light incident on the eye and retroreflected from the fundus of the eye using the apparatus in FIG. 45.

FIG. 46 shows a Poincaré sphere representation of the polarization state of the light in FIG. 45 as the polarization state is changed by typical amounts upon retroreflection from the annularly-scanned areas of the fundus of eye 477. Point 485 represents the initial state of polarization of the light incident on eye 477; left-hand circularly polarized light, with $S_3=-1$. Point 486 represents the polarization state that the light beam retroreflected from eye 477 would have in the absence of retinal nerve fiber birefringence. However, with the retinal nerve fiber birefringence acting and with the eye 477 fixating exactly in the center of the three-degree annular scan, the polarization state 487 of the retroreflected light will typically follow an elliptical path 488 around point 486. For each rotation of the scanned spot of light on the retina, the final polarization state will travel twice around path 488. With the Stokes parameter $S_3$ of the polarization state being measured by the apparatus in FIG. 45, a periodic signal will be obtained with frequency $2f_s$, exactly twice the spinning frequency ($f_s$) of the scan. However, if the eye is not fixating near the center of the annular scan, the periodic signal of the Stokes parameter $S_3$ will lose most or all of its $2f_s$ component and will gain significant $f_s$ components as well as other components that are harmonics of $f_s$.

As shown in the Poincaré sphere representation in FIG. 46, the orientation of the corneal birefringence is responsible for the longitude of the location of the ellipse of polarization states being measured. Using the Stokes parameter $S_3$ to assess the changes in the polarization state that occur with each scan results in a uniform signal being obtained regardless of the orientation of the corneal birefringence. If $S_1$ or $S_2$ alone were used, the amplitude of the periodic signal obtained would be strongly dependent on the orientation of the corneal birefringence. Thus, the measurement of Stokes parameter $S_3$, as a measure related to the ellipticity of the retroreflected light, significantly reduces interference in the measurement from the corneal birefringence.

Figure 47:
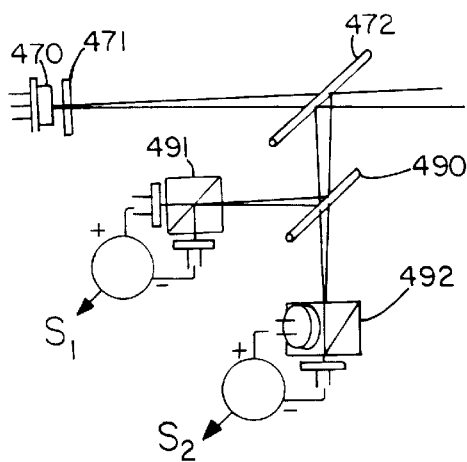
FIG. 47 is a diagram of an alternative embodiment of the illumination/detection system of the apparatus in FIG. 45 wherein polarization-related changes in the light retroreflected from the fundus of the eye are detected by measuring Stokes parameters $S_1$ and $S_2$ of the retroreflected light.

FIG. 47 shows an alternative differential polarization analyzer compared to the one shown in FIG. 45. Retroreflected light returning from eye 477 is partially reflected by non-polarizing beam splitter 472 as in FIG. 45, but in FIG. 47 the light is divided further by non-polarizing beam splitter 490 to pass to polarizing beam splitters 491 and 492. Polarizing beam splitters 491 and 492 each have two photodetectors associated with them for differential polarization measurement. The differential polarization measurement obtained with polarizing beam splitter 491 yields the Stokes parameter $S_1$. The differential polarization measurement obtained with polarizing beam splitter 492, rotated 45 degrees from the corresponding azimuth of polarizing beam splitter 491, yields the Stokes parameter $S_2$. By measuring $S_1$ and $S_2$ simultaneously during the annular scan, the projection 489 of path 488 in FIG. 46 onto the $S_1/S_2$ plane is obtained. The shape and angular size of this projection 489 are substantially independent of the orientation of the corneal birefringence when eye 477 is fixating precisely in the center of the annular scan. A periodic signal can be obtained from the simultaneous measurement of $S_1$ and $S_2$, for example, by calculating the instantaneous amplitude or angular orientation of the resultant vector of $S_1$ and $S_2$ in the $S_1/S_2$ plane. This periodic signal will be substantially independent of the orientation of the corneal birefringence when eye 477 is fixating exactly in the center of the annular scan, and will have a strong frequency component at $2f_s$, twice the scan frequency of $f_s$. However, if the eye is not fixating near the center of the annular scan, the periodic signal obtained will lose most or all of its $2f_s$ component and will gain significant $f_s$ components as well as other components that are harmonics of $f_s$.

Figure 48:
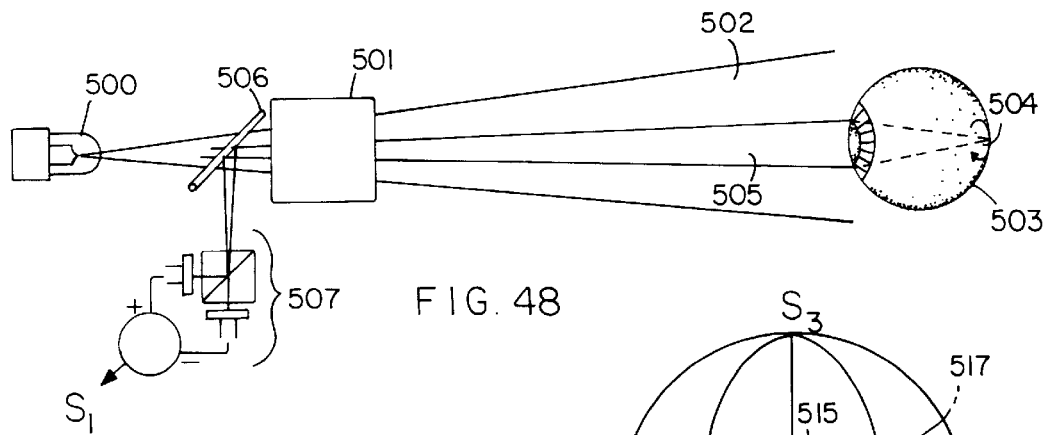
FIG. 48 is a diagram of an alternative embodiment of the present invention wherein non-polarized light is used as the light incident on the eye and polarization-related changes in the light retroreflected from the fundus of the eye are detected by measuring Stokes parameter $S_1$ of the retroreflected light.

FIG. 48 shows an alternative embodiment of the present invention which relies on the dichroism of the lutein pigment particles. These pigment particles are arrayed along the Henle fibers in the fovea and along the ends of the retinal nerve fibers closest to the fovea, as depicted in FIG. 3. Because the pigment particles 28 are aligned with the nerve fibers that they are arrayed upon, the polarization-related changes occurring when light double-passes through them have the same angular dependence as the polarization-related changes produced in polarized light by the birefringence of the retinal nerve fibers.

In FIG. 48, non-polarized light from spot light source 500 is used in a scanning arrangement similar to that in FIG. 45, except that the scanning system in FIG. 48 is shown schematically by box 501. The light 502 incident on eye 503 overfills the pupil of eye 503, and an image of the source is scanned in a small annulus on the retina of eye 503 as shown by circular arrow 504. Light beam 505, retroreflected from the fundus of eye 503, returns through the scanning system 501 to be partially reflected by non-polarizing beam splitter 506 to differential polarization analyzer 507. Differential polarization analyzer 507 includes a polarizing beam splitter and two photodetectors. The outputs of the two photodetectors are subtracted, yielding a value proportional to the Stokes parameter $S_1$ of the polarization state.

Since the light 502 incident on eye 503 is non-polarized, the corneal birefringence has no effect on this light as it passes through the cornea on its way to the retina. Likewise, if the beam of non-polarized light passes through retinal nerve fibers alone in the process of being retroreflected from the fundus of eye 503, it will remain non-polarized and pass out of the eye still in a non-polarized state. However, if the beam of non-polarized light passes through lutein pigment particles in the vicinity of the fovea, it will become partially linearly polarized by the double pass through the dichroic pigment particles and will be changed further in its state of polarization in passing through the corneal birefringence upon exiting the eye.

Figure 49:
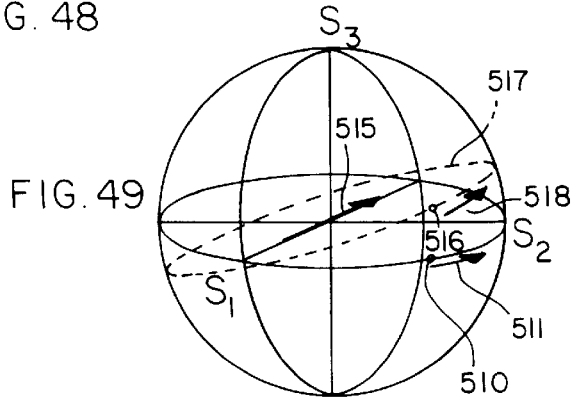
FIG. 49 is a Poincaré sphere showing representative final polarization states of the light retroreflected from the fundus of the eye using the apparatus in FIG. 48.

FIG. 49 shows a Poincaré sphere representation of the polarization states that the beam of non-polarized light acquires upon double-passing the lutein pigment particles, and the polarization states that the beam of light subsequently acquires upon exiting from the eye through the birefringent cornea. Point 510 on the equator of the Poincaré sphere in FIG. 49 represents a typical linear polarization state that the beam of light acquires upon double-passing the lutein pigment particles. If eye 503 is fixating directly in the center of circular scan 504, the lutein pigment particles that are encountered by the scan will be arranged precisely radially, along the Henle fibers in the fovea. The partial linear polarization acquired by the retroreflected beam of light will, therefore, rotate in its meridional orientation as the scan proceeds from one meridian to the next. This rotation of the azimuth of the state of linear polarization of the light can be represented as movement of the state of polarization along the equator of the Poincaré sphere in FIG. 49 in the direction of arrow 511, at an angular frequency of $2f_s$, twice the angular frequency ($f_s$) of the scan.

On passing out through the birefringent cornea of eye 503, the polarization state of the retrorcflected beam of light will be rotated approximately 30 degrees (the typical retardance of the corneal birefringence) about the eigenvector 515 in FIG. 49. The eigenvector 515 represents the linear retardance of the cornea. Polarization state 510 will thus be rotated to polarization state 516, and the final polarization states of the light 505 exiting the eye will follow along the path shown by 517 in the direction shown by arrow 518, at a frequency of $2f_s$.

As shown in FIG. 48, by measuring the Stokes parameter $S_1$ of the light retroreflected from the fundus of the eye, a periodic signal will be obtained which will have a strong frequency component at $2f_s$ if the eye 503 is precisely fixating in the center of scan 504. If fixation shifts away from the center of scan 504, the $2f_s$ frequency component of the periodic signal will decrease or disappear, frequency components at $f_s$ or harmonics of $f_s$ may appear, or the signal may disappear altogether if lutein pigment particles are no longer encountered by the retroreflected light beam.

As illustrated in the Poincaré sphere representation in FIG. 49, measurement of either the Stokes parameter $S_1$ or the Stokes parameter $S_2$ of the retroreflected light will give a periodic signal which can be somewhat influenced by the birefringence of the cornea because the birefringence of the cornea tilts path 517 away from the equator of the Poincaré sphere.

Figure 50:
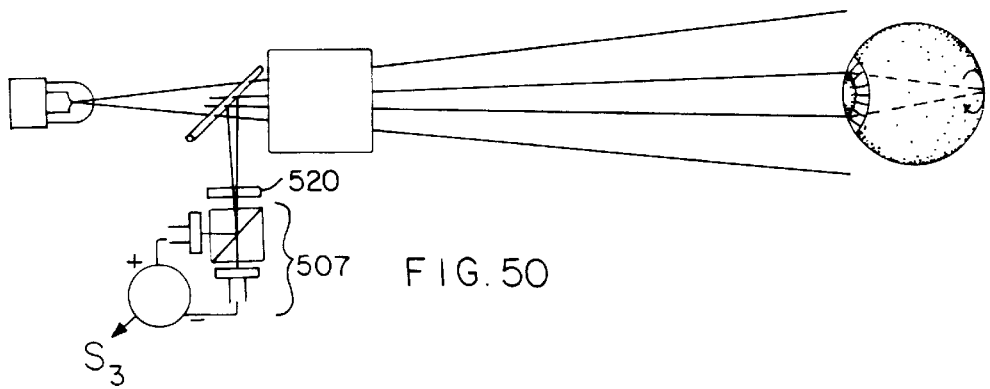
FIG. 50 is a diagram of an alternative embodiment of the present invention wherein non-polarized light is used as the light incident on the eye and polarization-related changes in the light retroreflected from the fundus of the eye are detected by measuring Stokes parameter $S_3$ of the retroreflected light.

FIG. 50 shows the same arrangement as FIG. 48 except that quarter wave plate 520 has been added before differential polarization analyzer 507. This addition yields the Stokes parameter $S_3$ as the measured value. A periodic signal will be obtained with this arrangement whose amplitude is sinusoidal and independent of the orientation of the corneal birefringence. However, this arrangement does depend on the presence of corneal birefringence to tilt the path 517 away from the equator of the Poincaré sphere in FIG. 49 so that a periodic signal can be obtained for the Stokes parameter $S_3$.

Figure 51:
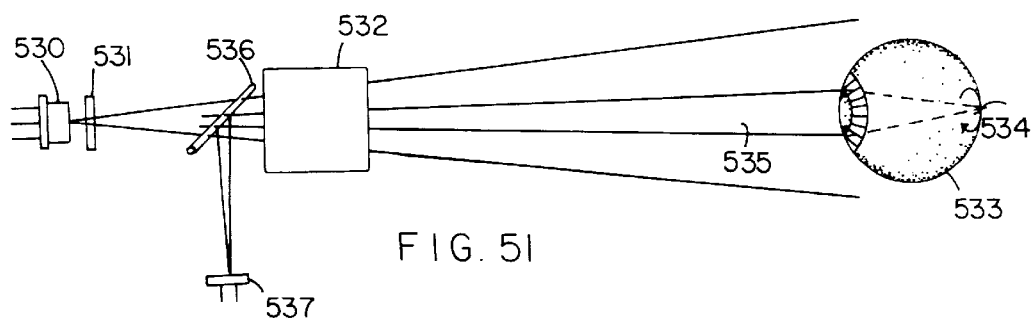
FIG. 51 is a diagram of an alternative embodiment of the present invention wherein polarization-related changes in the light retroreflected from the fundus of an eye are detected by measuring changes in the overall intensity of the retroreflected light.

FIG. 51 shows an alternative embodiment of the present invention, using a single photodetector to measure polarization-related changes in light retroreflected from the fundus of an eye. Laser diode 530 provides a beam of linearly polarized light which is converted to circularly polarized light by quarter wave plate 531. The light passes through scanning system 532, similar to scanning system 501 in the apparatus of FIG. 48, to be incident on eye 533. An image of light source 530 is then scanned in a circular scan 534 on the fundus of eye 533. Retroreflected light 535 is partially reflected by non-polarizing beam splitter 536 to be detected by photodetector 537. In this arrangement, the light striking the retina will have a constant, elliptical polarization state determined by the corneal birefringence acting upon the initially circularly polarized light. A component of the elliptically polarized light will be absorbed by the dichroic lutein pigment, with the amount absorbed depending on the relative orientation of the lutein pigment particles to the orientation of the elliptical polarization. As the light beam is scanned with the frequency $f_s$ in a circle exactly centered on the fovea, the orientation of the lutein pigment particles will rotate with the frequency of $2f_s$. The proportion of light absorbed by the dichroic effect of the lutein pigment will, therefore, fluctuate with the frequency of $2f_s$, varying the overall intensity of the light retroreflected from the eye with the same frequency. The intensity of the light retroreflected from the eye is measured by photodetector 537 in FIG. 51. Only when there is exact fixation of the eye 533 in the center of the scan will a $2f_s$ frequency component in the signal be obtained. If fixation wanders away from the center of scan 534, the $2f_s$ frequency component will decrease or disappear, frequency components at $f_s$ or harmonics of $f_s$ may appear, or the signal will disappear completely if lutein pigment particles are no longer encountered.

With the apparatus of FIG. 51, the use of circularly polarized light, which is independent of meridional orientation, and the detection of simple light intensity, which is independent of the orientation of the corneal birefringence, combine to provide a uniform signal that is largely free from interference from the corneal birefringence.

The embodiments of the present invention described herein can variously use visible light, ultraviolet light, or infrared light, provided that the optical media of the eye are relatively transparent to the wavelength of light used. In addition, most of the embodiments of the present invention involve the use of polarized incident light. Although polarized incident light produced by an infrared laser diode is predominantly used in the various embodiments of the present invention, it would be obvious to one skilled in the art that other sources of polarized light could be used. For example, other lasers with necessary polarizers may be used to obtain the proper type of polarized light. Furthermore, other light sources may also be used for some applications, including incandescent light sources, light-emitting diodes, super-luminescent diodes, and are lamp sources. The use of other light sources presupposes the use of necessary filters to isolate certain wavelength bands of light and necessary polarizers to provide the proper type of polarization.

It will also be obvious to one skilled in the art that numerous opto-mechanical modifications of the embodiments described herein continue to fall within the scope of the present invention. For example, various types of polarimeters known to the art can be substituted for the polarization-sensitive detectors illustrated here. Sophisticated opto-mechanical scanning systems may be used in place of the wobbling mirror scanning methods illustrated here. Integrated opto-electronic elements can combine emitters, beam splitters, and photodetectors into single compact assemblies. Objects other than the light sources and fixation marks of the illustrated embodiments may be used to advantage, particularly when the intended direction of fixation is in the center of a circularly scanned spot of light. Such objects can be flashed or otherwise modulated to attract attention. Annular areas of retina that are scanned may subtend visual angles smaller than, or larger than, three degrees. The eye fixation monitor embodiments illustrated here can also be conveniently combined with focus detecting optical systems, often sharing common optical elements, such that proper focus and proper fixation of the eye can be assessed simultaneously. For example, two versions of a focus-sensitive detecting system are illustrated in FIGS. 6 and 6a.

There are numerous applications for methods and apparatus used to assess the direction of fixation of an eye. For example, a detector of eye fixation can be coupled to a switch to enable visual remote control of external devices. An array of eye fixation monitors can be arranged in the form of a keyboard as a communication aid for the disabled. An array of fixation monitors can be optically superimposed via a beam splitter on any visual scene, to allow selection of menu items in that scene or for visual interaction with computer games. Automobile, aircraft, and industrial machinery controls can be activated remotely via eye fixation monitors. Any control currently operated manually, or by various forms of remote control including infrared light or ultrasound, can be operated via eye fixation monitors within a distance of at least several meters.

Interlock devices can be operated by visual fixation, such that a given direction of gaze can be guaranteed before operation of dangerous machinery. Fixation direction can be confirmed during various forms of eye testing such as visual field examination, or various forms of eye treatment such as laser eye surgery.

Tabulation of eye contacts with advertising material can be performed by eye fixation detection. Surveys of voting results by a group of people can be tabulated by counting the number of eye contacts made on designated displays.

Proper alignment of the eye can be confirmed with various apparatus used for identification purposes. For example, once eye alignment is confirmed by an eye fixation monitor, iris patterns, retina patterns, or scanned patterns of birefringence changes from the fundus can be used for identification purposes. An eye fixation monitor/scanner can serve as a universal identification card, "fingerprint," or credit card replacement. Such an identification function can be used to arm/disarm security devices, open doors, unlock computers, and perform other security functions.

Detection of fixation by both eyes simultaneously can be used to confirm normal binocular eye alignment, or alternatively to screen for eye misalignment (the clinical condition known as strabismus), especially in infants and young children.

By detecting the fixation direction of an eye and comparing it to a reference direction, an eye fixation monitor can be optically or mechanically moved under feedback control to accomplish eye tracking. Alternatively, wide-field arrays of polarization-sensitive detectors can be optically superimposed, via beam splitters on visual scenes to enable eye tracking by detecting the characteristic polarizationrelated changes caused by the fovea.

An eye tracking device based on the monitoring of eye fixation can be used to select items from visual menus, to guide computer cursors, to aim cameras, to aim weapons, to aim laser medical treatments, to guide scanning devices to record selected passages of written material, music, or check-out bar codes, to select objects on air traffic control screens or highway radar screens, to select targets on military fire control screens for radar lock-on, to guide motor vehicles or aircraft, and to visually interact with computer games and other displays.

Binocular eye tracking devices can be used for remote control manipulation of external devices, such as remote-controlled surgical instruments, industrial machinery, and the like. Binocular eye tracking can also be used for automatic measurement of the amount of misalignment of the eyes in various directions of gaze and to provide feedback regarding the positions of the eyes during eye alignment exercises and sports vision exercises.

Finally, the polarization-related changes recorded in the process of eye fixation monitoring can provide valuable information regarding the presence or progression of various forms of eye disease or aging processes that affect the fovea or other retinal areas.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An apparatus for assessing the fixation state of at least one eye, each eye having a corneal birefringence meridional direction, a fundus, a fovea having a projection, lutein pigment having a dichroic effect, and a fixation state, said apparatus comprising:

a) an illumination system, comprising at least one light source, for providing at least one beam of incident light to each of said at least one eye;

b) a detection system, synchronously operable with said illumination system and comprising at least one photodetector, each of said at least one photodetector comprising a detection surface, for detecting incident light reflected from the fundus of each of said at least one eye; and c) an analysis system, operably connected with both said illumination system and said detection system, for determining polarization-related changes that have occurred between the incident light and the reflected light and for assessing foveal projection information for each of said at least one eye from said polarization-related changes detected in the reflected light, wherein said foveal projection information indicates the fixation state of the eye, said fixation state of the eye varying from a fixated condition to a non-fixated condition.

2. The apparatus of claim 1 wherein said fixation state further comprises a direction of fixation.

3. The apparatus of claim 1 wherein said at least one light source is substantially conjugate to the plane of fixation of at least one eye.

4. The apparatus of claim 3 wherein said at least one beam of incident light is cyclically scanned across a portion of the fundus of the eye.

5. The apparatus of claim 4 wherein the detected polarization-related changes in the reflected light occur at a phase with respect to said cyclical scan of said at least one beam of incident light, wherein said phase is used to assess the direction of fixation of the eye.

6. The apparatus of claim 1 wherein said at least one photodetector is substantially conjugate to the plane of fixation of at least one eye, wherein said at least one photodetector may be selectively operable to receive a cyclical scan of reflected light from a portion of the fundus of the eye.

7. The apparatus of claim 6 wherein the detection system comprises an array of photodetectors, wherein the photodetectors in the array may be selectively interrogated to provide said cyclical scan.

8. The apparatus of claim 6 wherein the detection surface of each of said at least one photodetector may be selectively exposed to a portion of the incident light reflected from the fundus of the eye, wherein the selective exposure of the detection surface of each of said at least one photodetector provides said cyclical scan.

9. The apparatus of claim 8 wherein the detection system comprises an aperture for selectively exposing said detection surface of each of said at least one photodetector.

10. The apparatus of claim 6 wherein the detected polarization-related changes in the reflected light occur at a phase with respect to said cyclical scan, wherein said phase is used to assess the direction of fixation of the eye.

11. The apparatus of claim 1 wherein both said at least one light source and said at least one photodetector are substantially conjugate to the plane of fixation of at least one eye, wherein said at least one photodetector may be selectively operable to receive a cyclical scan of reflected light from a portion of the fundus of the eye.

12. The apparatus of claim 11 wherein said at least one light source and said at least one photodetector are substantially centered with respect to each other in substantially conjugate planes.

13. The apparatus of claim 12 wherein said at least one light source and said at least one photodetector are substantially conjugate with respect to each other in size and in axial location, providing sensitivity to eye defocus.

14. The apparatus of claim 11 wherein said at least one beam of incident light is cyclically scanned across a portion of the fundus of the eye.

15. The apparatus of claim 14 wherein the detected polarization-related changes in the reflected light occur at a phase with respect to said cyclical scan of said at least one beam of incident light, wherein said phase is used to assess the direction of fixation of the eye.

16. The apparatus of claim 11 wherein the detection system comprises an array of photodetectors, wherein the photodetectors in the array may be selectively interrogated to provide said cyclical scan.

17. The apparatus of claim 11 wherein the detection surface of each of said at least one photodetector may be selectively exposed to a portion of the incident light reflected from the fundus of the eye, wherein the selective exposure of the detection surface of said at least one photodetector provides said cyclical scan.

18. The apparatus of claim 17 wherein the detection system comprises an aperture for selectively exposing said detection surface of said at least one photodetector to a portion of the incident light reflected from the fundus of the eye.

19. The apparatus of claim 11 wherein the detected polarization-related changes in the reflected light occur at a phase with respect to said cyclical scan, wherein said phase is used to assess the direction of fixation of the eye.

20. The apparatus of claim 1 wherein the incident light is selected from the group consisting of infrared light, visible light, and ultraviolet light.

21. The apparatus of claim 1 wherein the detection system is selected from the group consisting of at least one photodetector, a polarimeter comprising at least one polarizing analyzer in combination with at least one photodetector, and an ellipsometer.

22. The apparatus of claim 1 further comprising an illumination path holographic optical element, wherein said illumination path holographic optical element directs the incident light from the illumination system to each of said at least one eye.

23. The apparatus of claim 1 further comprising a detection path holographic optical element, wherein said detection path holographic optical element directs the reflected light to the detection system.

24. The apparatus of claim 1 wherein the beam of incident light has a polarization state which is substantially independent of the corneal birefringence meridional direction.

25. The apparatus of claim 24 wherein the incident light is selected from the group consisting of substantially non-polarized light and substantially circularly polarized light.

26. The apparatus of claim 24 wherein the detected polarization-related changes in the incident light reflected from the fundus of each of said at least one eye are substantially independent of the corneal birefringence meridional direction.

27. The apparatus of claim 26 wherein the reflected light has a polarization state characterized by Stokes parameters $S_1$, $S_2$, and $S_3$.

28. The apparatus of claim 27 wherein the detection system measures Stokes parameter $S_3$.

29. The apparatus of claim 27 wherein the detection system measures at least two of said Stokes parameters.

30. The apparatus of claim 24 wherein the detection system measures the overall intensity of the reflected light to determine the magnitude of the dichroic effect of the lutein pigment on the reflected light.

31. The apparatus of claim 1 further comprising a field of view in known correspondence with said illumination system and said detection system, wherein said analysis system processes said foveal projection information obtained from said at least one eye with respect to the field of view and produces a two-dimensional polarization-modulated image of the fundus of the eye, wherein said polarization-modulated image of the fundus is in known correspondence with the field of view and comprises the projection of the fovea.

32. The apparatus of claim 31 further comprising a display, wherein a visual identification of the projection of the fovea with respect to the field of view is produced on said display, said visual identification resulting from coordinate superimposition of a two-dimensional representation of the field of view and said polarization-modulated image of the fundus.

33. A method for assessing the fixation state of at least one eye, each eye having a corneal birefringence meridional direction, a fundus, a fovea, lutein pigment having a dichroic effect, and a fixation state, comprising the steps of:
  a) producing and directing at least one beam of incident light from an illumination system, said illumination system comprising at least one light source, toward each of said at least one eye to illuminate the area of the fundus of the eye which is aligned with said at least one beam of incident light;
  b) isolating and detecting light reflected from the illuminated area of the fundus of each of said at least one eye by a detection system, said detection system comprising at least one photodetector, each of said at least one photodetector comprising a detection surface;
  c) determining polarization-related changes that have occurred between the incident light and the reflected light; and
  d) correlating the polarization-related changes that are observed with polarization-related changes known to occur with known fixation states of the eye in order to determine fixation state information for each of said at least one eye, wherein said fixation state varies from a fixated condition to a non-fixated condition.

34. The method of claim 33 wherein said fixation state further comprises a direction of fixation.

35. The method of claim 33 wherein the step of producing and directing the incident light toward each of said at least one eye comprises aligning said at least one light source such that it is substantially conjugate to the plane of fixation of at least one eye.

36. The method of claim 35 further comprising the step of cyclically scanning said at least one beam of incident light across a portion of the fundus of the eye.

37. The method of claim 36 wherein the step of isolating and detecting the light reflected from each of said at least one eye comprises using the phase with which the detected polarization-related changes occur in the reflected light, with respect to the scan cycle of said at least one beam of incident light, to assess the direction of fixation of the eye.

38. The method of claim 33 wherein the step of isolating and detecting the reflected light from each of said at least one eye comprises aligning said at least one photodetector such that it is substantially conjugate to the plane of fixation of at least one eye, wherein said at least one photodetector may be selectively operable to receive a cyclical scan of reflected light from a portion of the fundus of the eye.

39. The method of claim 38 wherein the detection system comprises an array of photodetectors and said photodetectors in said array may be selectively interrogated to provide said cyclical scan.

40. The method of claim 38 further comprising the step of selectively exposing the detection surface of each of said at least one photodetector to a portion of the incident light reflected from the fundus of the eye, wherein the selective exposure of the detection surface of each of said at least one photodetector provides said cyclical scan.

41. The method of claim 40 further comprising the step of using an aperture to selectively expose the detection surface of each of said at least one photodetector.

42. The method of claim 38 further comprising the step of using the phase with which the detected polarization-related changes occur in the reflected light, with respect to said cyclical scan, to assess the direction of fixation of the eye.

43. The method of claim 33 wherein the step of producing and directing the incident light toward each of said at least one eye comprises aligning said at least one light source such that it is substantially conjugate to the plane of fixation of at least one eye and the step of isolating and detecting the reflected light from each of said at least one eye comprises aligning said at least one photodetector such that it is substantially conjugate to the plane of fixation of at least one eye, wherein said at least one photodetector may be selectively operable to receive a cyclical scan of reflected light from a portion of the fundus of the eye.

44. The method of claim 43 wherein said at least one light source and said at least one photodetector are substantially centered with respect to each other in substantially conjugate planes.

45. The method of claim 44 wherein said at least one light source and said at least one photodetector are substantially conjugate with respect to each other in size and in axial location to provide sensitivity to eye defocus.

46. The method of claim 43 further comprising the step of cyclically scanning said at least one beam of incident light across a portion of the fundus of the eye.

47. The method of claim 46 wherein the step of determining polarization-related changes that have occurred between the incident light and the reflected light comprises using the phase with which the detected polarization-related changes occur in the reflected light, with respect to the scan cycle of said at least one beam of incident light, to assess the direction of fixation of the eye.

48. The method of claim 43 wherein the detection system comprises an array of photodetectors and said photodetectors in said array may be selectively interrogated to provide said cyclical scan.

49. The method of claim 43 further comprising the step of selectively exposing the detection surface of each of said at least one photodetector to a portion of the incident light reflected from the fundus of the eye, wherein the selective exposure of the detection surface of each of said at least one photodetector provides said cyclical scan.

50. The method of claim 49 further comprising the step of using an aperture to selectively expose the detection surface of each of said at least one photodetector.

51. The method of claim 43 further comprising the step of using the phase with which the detected polarization-related changes occur in the reflected light, with respect to said cyclical scan, to assess the direction of fixation of the eye.

52. The method of claim 33 wherein the step of producing and directing the incident light toward each of said at least one eye comprises selecting the incident light from the group consisting of infrared light, visible light, and ultraviolet light.

53. The method of claim 33 wherein the detection system is selected from the group consisting of at least one photodetector, a polarimeter comprising at least one polarizing analyzer in combination with at least one photodetector, and an ellipsometer.

54. The method of claim 33 wherein the step of producing and directing the incident light toward each of said at least one eye comprises directing the incident light from the illumination system using a holographic optical element.

55. The method of claim 33 wherein the step of isolating and detecting the reflected light from each of said at least one eye comprises directing the reflected light to the detection system using a holographic optical element.

56. The method of claim 33 wherein the step of producing and directing the incident light toward each of said at least one eye comprises producing a beam of incident light which has a polarization state which is substantially independent of the corneal birefringence meridional direction.

57. The method of claim 56 wherein the incident light is selected from the group consisting of substantially non-polarized light and substantially circularly polarized light.

58. The method of claim 56 wherein the step of isolating and detecting the reflected light from each of said at least one eye comprises measuring polarization-related changes that are substantially independent of the corneal birefringence meridional direction of each of said at least one eye.

59. The method of claim 58 wherein the reflected light has a polarization state characterized by Stokes parameters $S_1$, $S_2$, and $S_3$.

60. The method of claim 59 further comprising the step of measuring Stokes parameter $S_3$.

61. The method of claim 59 further comprising the step of measuring at least two of said Stokes parameters.

62. The method of claim 56 wherein the step of isolating and detecting the reflected light from each of said at least one eye comprises measuring the overall intensity of the reflected light to determine the magnitude of the dichroic effect of the lutein pigment on the reflected light.

63. The method of claim 33 further comprising the step of producing a two-dimensional polarization-modulated image of the fundus of the eye, wherein said polarization-modulated image of the fundus is in known correspondence with a field of view and comprises the projection of the fovea, from the fixation state information of said at least one eye with respect to said field of view, wherein said field of view is in known correspondence with said illumination system and said detection system.

64. The method of claim 63 further comprising the step of producing a visual identification of the projection of the fovea with respect to the field of view on a display, said visual identification resulting from coordinate superimposition of a two-dimensional representation of the field of view and said polarization-modulated image of the fundus.

* * * * *

UNITED STATES PATENT AND TRADEMARK OFFICE
CERTIFICATE OF CORRECTION

PATENT NO. : 6,027,216
DATED : February 22, 2000
INVENTOR(S) : Guyton et al.

It is certified that error appears in the above-identified patent and that said Letters Patent is hereby corrected as shown below:

Title page,
Item [73] Assignee, after "Johns" insert -- Hopkins --.
Item [57] ABSTRACT, line 10, "rctroreflected" should raed -- retroreflected --.
Item [56] References Cited, OTHER PUBLICATIONS, "Optics" should read -- Optics --; "(1900)" should read -- (1990) --; "Blokland et al." should read -- Van Blokland et al. --.

Drawings,
Sheet 4 of 17, FIG. 9 should read:

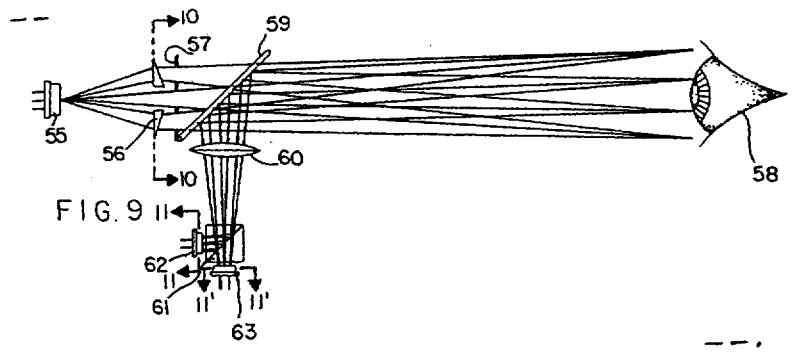

Sheet 5 of 17, FIG. 15 should read:

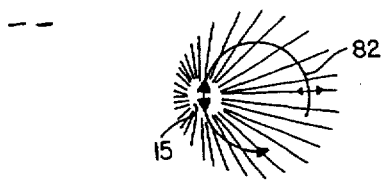

UNITED STATES PATENT AND TRADEMARK OFFICE
CERTIFICATE OF CORRECTION

PATENT NO. : 6,027,216
DATED : February 22, 2000
INVENTOR(S) : Guyton et al.

Page 2 of 7

It is certified that error appears in the above-identified patent and that said Letters Patent is hereby corrected as shown below:

Sheet 8 of 17, FIG. 22 should read:

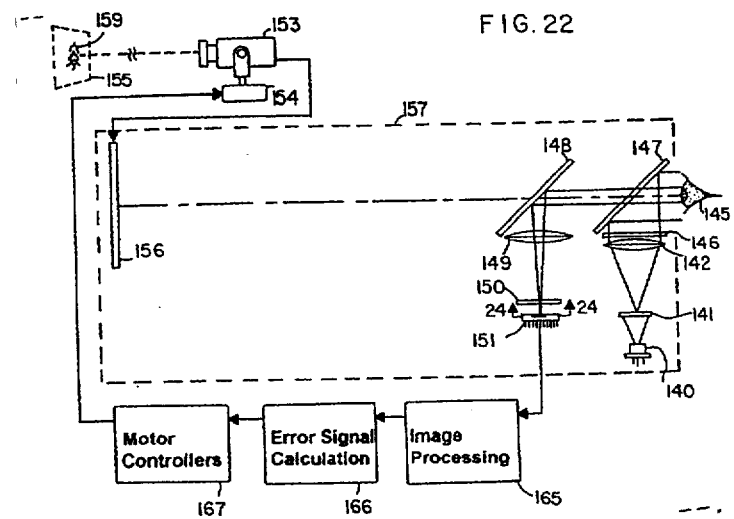

Sheet 8 of 17, FIG. 22a should read:

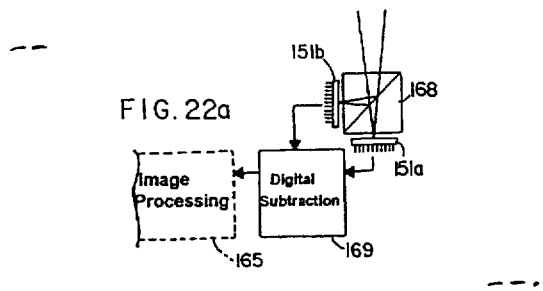

UNITED STATES PATENT AND TRADEMARK OFFICE
CERTIFICATE OF CORRECTION

PATENT NO. : 6,027,216  
DATED : February 22, 2000  
INVENTOR(S) : Guyton et al.

Page 3 of 7

It is certified that error appears in the above-identified patent and that said Letters Patent is hereby corrected as shown below:

Sheet 9 of 17, FIG. 29 should read:

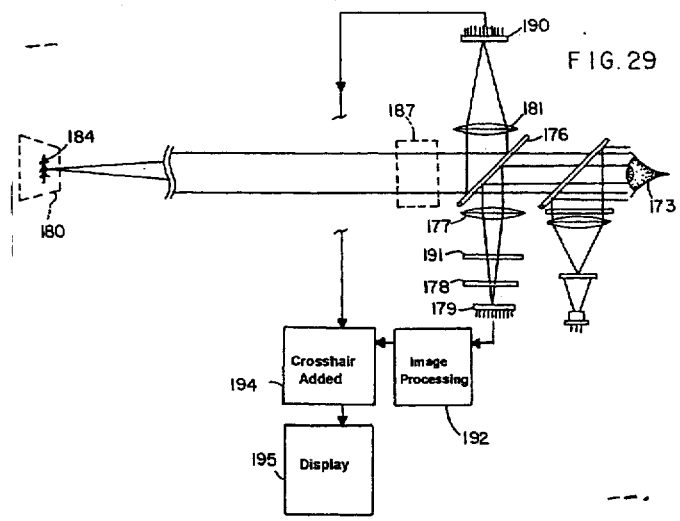

FIG. 33a and FIG. 33b should read:

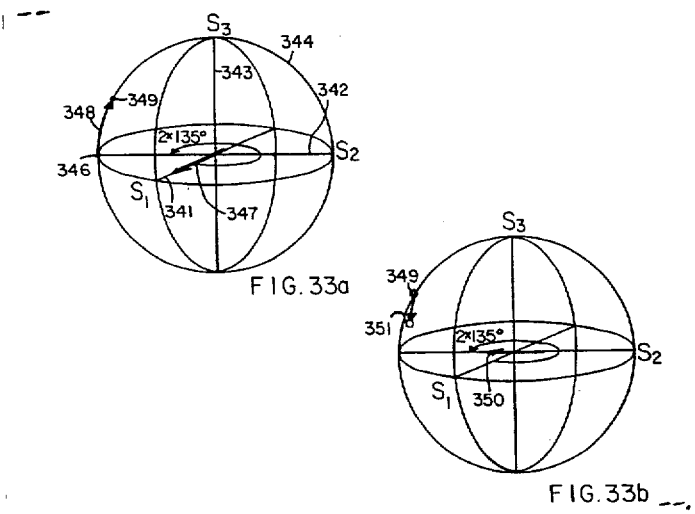

UNITED STATES PATENT AND TRADEMARK OFFICE
CERTIFICATE OF CORRECTION

PATENT NO. : 6,027,216
DATED : February 22, 2000
INVENTOR(S) : Guyton et al.

Page 4 of 7

It is certified that error appears in the above-identified patent and that said Letters Patent is hereby corrected as shown below:

Sheet 13 of 17, FIG. 38 should read:

--

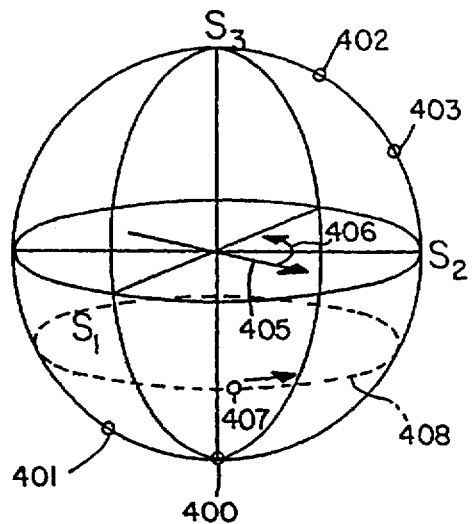

FIG. 38

-- .

Figure 42:
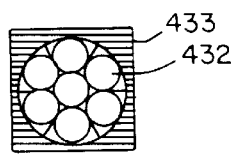
FIG. 42 is a diagram of a section taken through line 42—42 of FIG. 41, showing the various elements of the faceted prism.

Sheet 15 of 17, FIG. 42 should read:

--

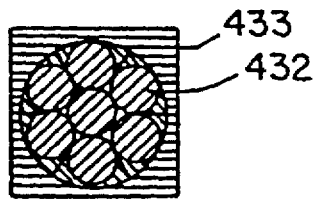

FIG. 42    -- .

UNITED STATES PATENT AND TRADEMARK OFFICE
CERTIFICATE OF CORRECTION

PATENT NO. : 6,027,216
DATED : February 22, 2000
INVENTOR(S) : Guyton et al.

It is certified that error appears in the above-identified patent and that said Letters Patent is hereby corrected as shown below:

Column 2,
Line 15, "comeal" should read -- corneal --.

Column 3,
Line 32, "Appi." should read -- Appl. --.

Column 4,
Line 37, "ftndus" should read -- fundus --.

Column 8,
Line 61, "retrorcflected" should read -- retroreflected --.

Column 9,
Line 40, "comeal" should read -- corneal --.

Column 10,
Line 12, "wlich" should read -- which --;
Line 28, "SI" should read -- $S_i$ --;
Line 34, "retinalbirefringence-induced" should read -- retinal-birefringence-induced --;
Line 53, "findus" should read -- fundus --.

Column 12,
Line 66, "comeal" should read -- corneal --;
Line 66, "unifonn" should read -- uniform --;
Line 67, "comeal" should read -- corneal --.

Column 14,
Line 10, cancel "which".

Column 16,
Line 15, "comeal" should read -- corneal --;
Line 17, "comeal" should read -- corneal --.

UNITED STATES PATENT AND TRADEMARK OFFICE
CERTIFICATE OF CORRECTION

PATENT NO.   : 6,027,216
DATED         : February 22, 2000
INVENTOR(S)   : Guyton et al.

It is certified that error appears in the above-identified patent and that said Letters Patent is hereby corrected as shown below:

Column 18,
Line 58, "polarizationrelated" should read -- polarization-related --.

Column 19,
Line 64, "the" should read -- The --.

Column 20,
Lines 43, 49, 50, 56 and 65, "FIG. 162" should read -- figure 162 --.

Column 21,
Lines 15-16, "pixalby-pixel" should read -- pixel-by-pixel --;
Line 62, "FIG. 186" should read -- figure 186 --.

Column 23,
Line 67, "comeal" should read -- corneal --.

Column 24,
Line 21, "$^{2+S}$" should read -- $^2$+S --;
Lines 45 and 51, "cigenvector" should read -- eigenvector --;
Line 55, "comeal" should read -- corneal --.

Column 25,
Line 53, "unifonn" should read -- uniform --.

Column 26,
Line 25, "ftndus" should read -- fundus --;
Line 27, "birefringenee" should read -- birefringence --.

Column 27,
Line 5, after "frequency" insert -- $f$. --.

Column 31,
Line 62, "$2\eta_s$," should read -- $2f_s$ --.

UNITED STATES PATENT AND TRADEMARK OFFICE
CERTIFICATE OF CORRECTION

PATENT NO. : 6,027,216
DATED : February 22, 2000
INVENTOR(S) : Guyton et al.

It is certified that error appears in the above-identified patent and that said Letters Patent is hereby corrected as shown below:

Column 32,
Line 58, "comeal" should read -- corneal --.

Column 35,
Line 15, "are" should read -- arc --.

Column 36,
Lines 22-23, "polarizationre-lated" should read -- polarization-related --.

Column 38,
Line 21, "thc" should read -- the --;
Line 44 and line 51, "comeal", each occurrence, should read -- corneal --.

Column 39,
Line 15, "comeal" should read -- corneal --.

Signed and Sealed this

Twenty-fifth Day of December, 2001

Attest:

Attesting Officer

JAMES E. ROGAN
Director of the United States Patent and Trademark Office